US009456748B2

(12) United States Patent
Imamura

(10) Patent No.: US 9,456,748 B2
(45) Date of Patent: Oct. 4, 2016

(54) OPHTHALMOLOGICAL APPARATUS, ALIGNMENT METHOD, AND NON-TRANSITORY RECORDING MEDIUM

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 341 days.

(21) Appl. No.: 14/140,674

(22) Filed: Dec. 26, 2013

(65) Prior Publication Data

US 2014/0185009 A1 Jul. 3, 2014

(30) Foreign Application Priority Data

Dec. 28, 2012 (JP) ................................. 2012-287253

(51) Int. Cl.
*A61B 3/14* (2006.01)
*A61B 3/15* (2006.01)
*A61B 3/00* (2006.01)
*A61B 3/10* (2006.01)

(52) U.S. Cl.
CPC ............. *A61B 3/152* (2013.01); *A61B 3/0025* (2013.01); *A61B 3/1025* (2013.01)

(58) Field of Classification Search
CPC .......... A61B 3/13; A61B 3/14; A61B 3/152; A61B 19/5223; G02B 21/0012
USPC ................................................ 351/200–247
See application file for complete search history.

(56) References Cited

U.S. PATENT DOCUMENTS

| 2007/0070295 | A1 | 3/2007 | Tsukada et al. |
| 2010/0277692 | A1 | 11/2010 | Mukai et al. |
| 2011/0026035 | A1 | 2/2011 | Muto et al. |
| 2014/0072232 | A1* | 3/2014 | Zheng ................... G06T 3/4053 382/199 |
| 2015/0172567 | A1* | 6/2015 | Ekeroth ................. H04N 5/332 348/82 |

FOREIGN PATENT DOCUMENTS

| CN | 1579320 A | 2/2005 |
| CN | 1939208 A | 4/2007 |
| CN | 101254090 A | 9/2008 |
| CN | 101986185 A | 3/2011 |
| EP | 2497413 A1 | 9/2012 |
| JP | H04-141131 A | 5/1992 |
| JP | H08-224213 A | 9/1996 |
| JP | 2007-117714 A | 5/2007 |
| JP | 2009-276327 A | 11/2009 |
| JP | 2010-259543 A | 11/2010 |
| WO | 2012/026597 A1 | 3/2012 |

* cited by examiner

*Primary Examiner* — Mahidere Sahle
(74) *Attorney, Agent, or Firm* — Canon U.S.A. Inc., IP Division

(57) ABSTRACT

An ophthalmological apparatus includes an image acquisition unit configured to acquire images of different magnifications, a decision unit configured to decide, based on at least the acquired images or capture conditions of the acquired images, a method for capturing an image of an intermediate magnification that is between the magnifications of the acquired images, and an alignment unit configured to align the acquired images.

13 Claims, 17 Drawing Sheets

OPHTHALMOLOGICAL APPARATUS, ALIGNMENT METHOD, AND NON-TRANSITORY RECORDING MEDIUM

BACKGROUND OF THE INVENTION

1. Field of the Invention

The present invention relates to an ophthalmological apparatus and an alignment method.

2. Description of the Related Art

An eye examination is widely performed for the purpose of early diagnosis of lifestyle-related diseases and diseases ranked high as causes of blindness. Scanning laser ophthalmoscopes (SLOs), which are ophthalmological apparatuses based on the principle of confocal laser scanning microscopy, are apparatuses that perform a raster scan on the fundus with a laser beam serving as measurement light and capture a high-resolution plane image at a high speed on the basis of the intensity of the returning light.

Hereinafter, an apparatus that captures such a plane image is referred to as an SLO apparatus and the plane image is referred to as an SLO image.

Recently, it has become possible to capture SLO images of the retina with an improved lateral resolution by increasing the diameter of a measurement light beam in SLO apparatuses. However, the increased diameter of the measurement light beam has caused, when SLO images of the retina are captured, an issue of decreased signal-to-noise (S/N) ratio and resolution of the SLO images due to the aberrations of the subject's eye.

To address this issue, adaptive optics SLO apparatuses have been developed. Adaptive optics SLO apparatuses include an adaptive optics system configured to measure, with a wavefront sensor, the aberrations of a subject's eye in real time and to correct, with a wavefront correction device, the aberrations of measurement light and its returning light caused by the subject's eye. Such adoptive optics SLO apparatuses can capture SLO images with a high lateral resolution.

In order to capture such high-lateral-resolution SLO images as a moving image and noninvasively observe blood flow, for example, retinal blood vessels are extracted from each frame and the speed at which blood cells move in capillaries or the like is measured. Also, in order to evaluate the relationship between the visual performance and a density distribution or array of photoreceptor cells P using SLO images, the photoreceptor cells P are detected and the density distribution or array of the photoreceptor cells P is measured. FIG. 6B illustrates an example of a high-lateral-resolution SLO image. The photoreceptor cells P, a low-luminance region Q which represents positions of capillaries, and a high-luminance region W which represents a position of a white blood cell are observable.

When the photoreceptor cells P are observed or the distribution of the photoreceptor cells P is measured in the SLO image, an in-focus position is set to be in the vicinity of the retinal outer layer (B5 in FIG. 6A). In this state, an SLO image such as the one illustrated in FIG. 6B is captured. Along the retinal inner layers (B2 to B4 in FIG. 6A), retinal blood vessels and capillaries branching from the retinal blood vessels run.

As an alignment technique applied to a low-magnification image Dl and a high-magnification image Dh of the eye, a technique for displaying a capture position of an adaptive optics SLO image on a low-magnification image of the fundus is disclosed in Japanese Patent Laid-Open No. 2010-259543.

When a high-lateral-resolution image (high-magnification image Dh) is superimposed on a wide-angle image (low-magnification image Dl) (see FIG. 6C), alignment is sometimes not accurately achieved because these images lack a common image feature owing to their greatly different angles of view and pixel sizes.

Accordingly, a technique is desired which allows for accurate alignment of images that have greatly different angles of view and pixel sizes by capturing an intermediate-magnification image Dm including an image feature in common with the high-magnification image Dh and an image feature in common with the low-magnification image Dl and by performing alignment using the intermediate-magnification image Dm.

Also, as illustrated in FIG. 6D, a capture position or capture range of a tomographic image is sometimes superimposed on the low-magnification image Dl of the eye. The resulting image is typically displayed along with the tomographic image (FIG. 6A) and is used to observe a layer shape of the eye while checking the capture position of the tomographic image.

If the high-magnification image Dh is accurately aligned on the low-magnification image Dl, the capture position of the tomographic image can be superimposed on the high-magnification image Dh. This thus makes it possible to observe and analyze a relationship between a distribution of the photoreceptor cells P in the high-magnification image Dh (for example, a range of defective photoreceptor cells) and the layer shape of the eye (for example, thinning of the retinal outer layer).

In addition to the capture position of the tomographic image, i) a distribution of layer shape values (FIG. 6E), ii) a distribution of retina sensitivity values (FIG. 6F), and iii) a position irradiated with a therapeutic laser beam are sometimes superimposed on the low-magnification image Dl of the eye. If the high-magnification image Dh is accurately aligned on the low-magnification image Dl, a relationship between an image feature in the high-magnification image Dh and these pieces of information can be observed and analyzed. For example, when the information i) is used, a relationship between a distribution of the retinal outer layer thickness and a density distribution of photoreceptor cells can be observed and analyzed. When the information ii) is used, a relationship between a distribution of visual performance measurement values and a density distribution of photoreceptor cells can be observed and analyzed. When the information iii) is used, a relationship between a treatment-target site and a distribution of capillaries or a blood flow speed can be observed and analyzed.

The technique disclosed in Japanese Patent Laid-Open No. 2010-259543 uses a tracking technique to associate relative positions of the low-magnification image Dl and the high-magnification image Dh with each other. However, Japanese Patent Laid-Open No. 2010-259543 does not disclose any image-processing-based alignment technique which also addresses the case of subjects with unstable fixation.

Japanese Patent Laid-Open No. 2009-276327 discloses a technique for alignment and display of a cell image captured with a full-field optical coherence tomography (OCT) and a low-magnification image of the fundus. However, Japanese Patent Laid-Open No. 2009-276327 does not disclose any image-processing-based alignment technique which also addresses the case where images having greatly different pixel sizes lack a common image feature and the case of subjects with unstable fixation.

Japanese Patent Laid-Open No. 2007-117714 discloses a technique for displaying a capture position of a tomographic image on an image of the fundus. However, Japanese Patent Laid-Open No. 2007-117714 does not disclose any technique for displaying a capture position of a tomographic image or a retina sensitivity distribution on the high-resolution image Dh of cells.

SUMMARY OF THE INVENTION

The present invention has been made in view of the above-described drawbacks, and aims for accurate alignment of images of an eye that have greatly different angles of view or pixel sizes.

To this end, for example, an ophthalmological apparatus according to an aspect of the present invention includes an image acquisition unit configured to acquire images of different magnifications, a decision unit configured to decide, based on at least the acquired images or capture conditions of the acquired images, a method for capturing an image of an intermediate magnification that is between the magnifications of the acquired images, and an alignment unit configured to align the acquired images.

Also, an image processing method according to another aspect of the present invention includes acquiring ophthalmological images of different magnifications; deciding, based on at least the acquired ophthalmological images or capture conditions of the acquired ophthalmological images, a method for capturing an ophthalmological image of an intermediate magnification that is between the magnifications of the acquired ophthalmological images; and performing alignment of the acquired ophthalmological images.

Further features of the present invention will become apparent from the following description of exemplary embodiments with reference to the attached drawings.

DESCRIPTION OF THE EMBODIMENTS

An ophthalmological apparatus and an alignment method according to embodiments of the present invention will be described in detail below with reference to the accompanying drawings. Note that the present invention is not limited to these embodiments.

First Embodiment

An ophthalmological apparatus according to a first embodiment acquires an adaptive optics SLO image which serves as a high-magnification image Dh and an SLO image of an eye which serves as a low-magnification image Dl and on which a scanning position of an eye tomographic image is superimposed. The ophthalmological apparatus determines whether an intermediate-magnification image Dm needs to be acquired and determines a capture magnification and a capture position at which the intermediate-magnification image Dm is to be captured, on the basis of a difference in magnification between the high-magnification image Dh and the low-magnification image Dl and a fixation position used for the high-magnification image Dh. The ophthalmological apparatus acquires the intermediate-magnification image Dm if needed. The ophthalmological apparatus then performs alignment of images having close magnifications sequentially from the image having the lowest magnification, on the basis of an image feature that is common to the images. In this way, the ophthalmological apparatus decides a relative position of the high-magnification image Dh on the low-magnification image Dl.

Through this process, images of an eye that have greatly different angles of view or pixel sizes may be accurately aligned.

In the first embodiment, a case where a scanning position of an eye tomographic image displayed on the low-magnification image Dl is superimposed on the high-magnification image Dh will be described as an example of displaying aligned images of the eye that have greatly different angles of view and pixel sizes.

Overall Configuration

Figure 2A:
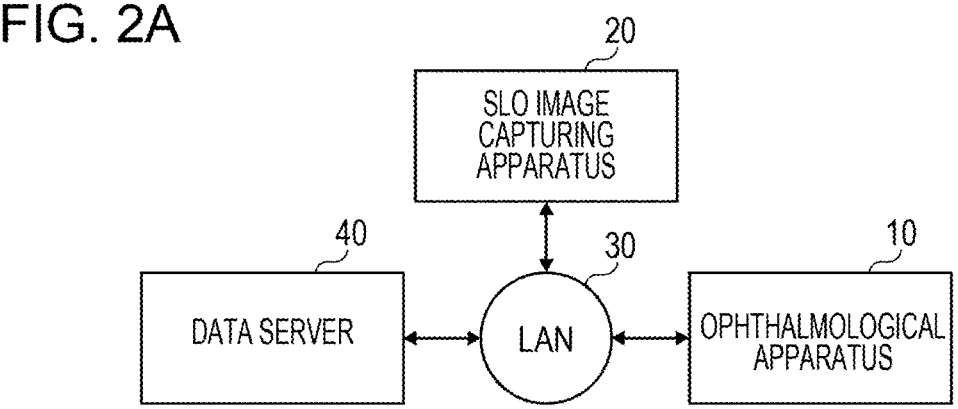
FIGS. 2A to 2C are block diagrams illustrating examples of the configuration of a system including the ophthalmological apparatus.

FIG. 2A is a diagram illustrating the configuration of a system including the ophthalmological apparatus 10 according to the first embodiment. As illustrated in FIG. 2A, the ophthalmological apparatus 10 is connected to an SLO image capturing apparatus 20 and a data server 40 via a local area network (LAN) 30, which is constructed using an optical fiber, Universal Serial Bus (USB), or IEEE 1394 interface. The ophthalmological apparatus 10 may be connected to these apparatuses via an external network, such as the Internet, or may be connected directly to the SLO image capturing apparatus 20.

The SLO image capturing apparatus 20 is an apparatus that captures the low-magnification image Dl, the intermediate-magnification image Dm, and the high-magnification image Dh of an eye. The SLO image capturing apparatus 20 captures the low-magnification image Dl, the intermediate-magnification image Dm, and the high-magnification image Dh. The SLO image capturing apparatus 20 then transmits the low-magnification image Dl, the intermediate-magnification image Dm, and the high-magnification image Dh and information of fixation positions Fl, Fm, and Fh respectively used during capturing of the low-magnification image Dl, the intermediate-magnification image Dm, and the high-magnification image Dh to the ophthalmological apparatus 10 and the data server 40.

Note that "m" denotes the magnification number and a relationship "l<m<h" is satisfied. Also, in the case where images of respective magnifications are captured at different positions, the captured images are denoted using Dli, Dmj, and Dhk. That is, "i", "j", and "k" are variables denoting the capture position numbers. The variables i, j, and k are defined as follows: i=1, 2, ..., imax; j=1, 2, ..., jmax; and k=1, 2, ..., kmax.

The data server 40 holds therein the low-magnification image Dl, intermediate-magnification image Dm, and high-magnification image Dh of a subject's eye; and the fixation positions Fl, Fm, and Fh respectively used during capturing of the low-magnification image Dl, intermediate-magnification image Dm, and high-magnification image Dh. The data server 40 also holds therein a list of image features observed at the respective capture magnifications of the images and a map indicating a probability of existence of a large image feature. The data server 40 stores therein the low-magnification image Dl, intermediate-magnification image Dm, and high-magnification image Dh and the fixation positions Fl, Fm, and Fh used during capturing of the corresponding images that are output by the SLO image capturing apparatus 20. The data server 40 also transmits, in response to a request received from the ophthalmological apparatus 10, the low-magnification image Dl, the intermediate-magnification image Dm, and the high-magnification image Dh; the fixation positions Fl, Fm, and Fh; the list of image features observed at the respective magnifications of the images; and the image feature existence probability map to the ophthalmological apparatus 10.

Figure 1:
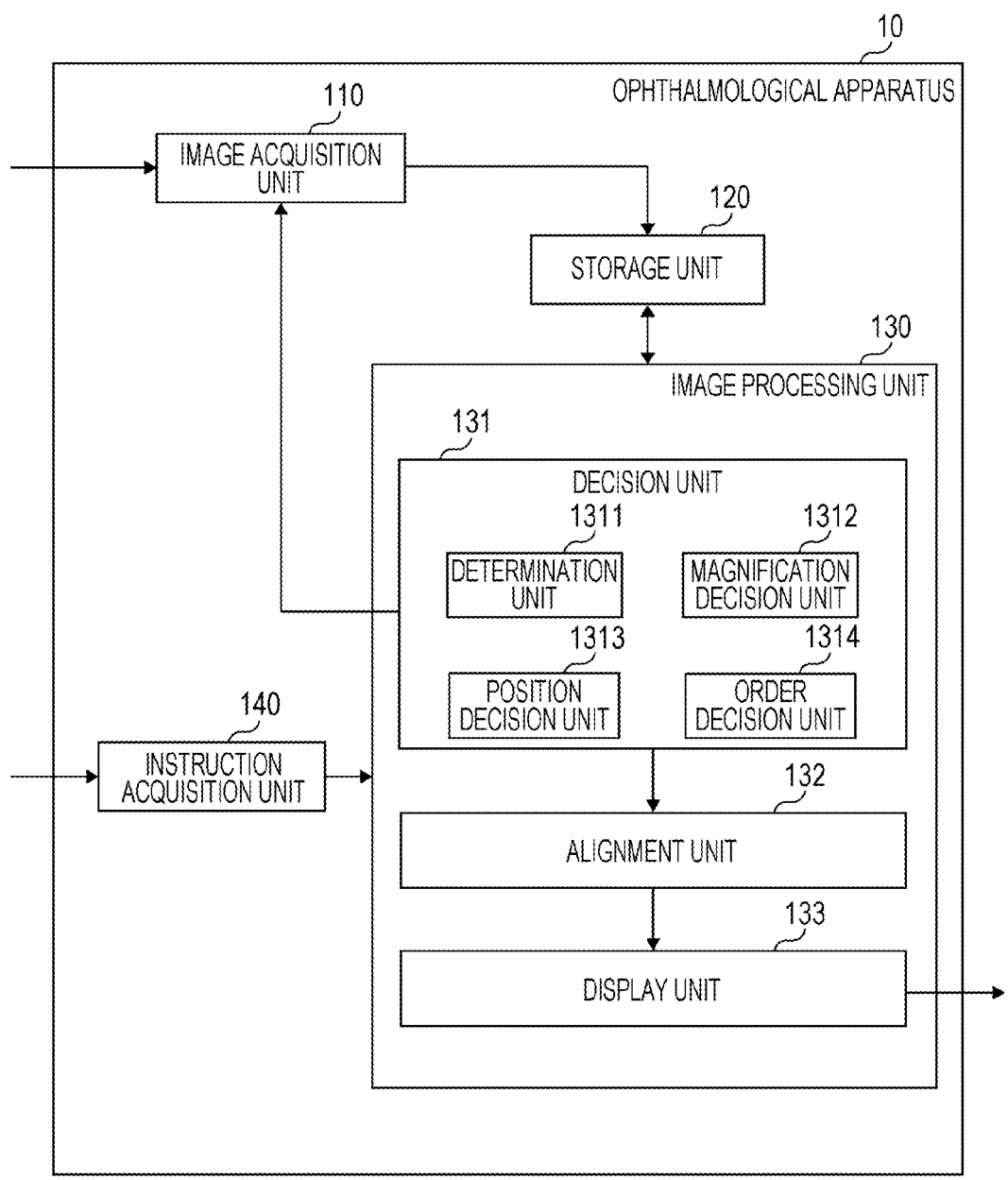
FIG. 1 is a block diagram illustrating an example of the functional configuration of an ophthalmological apparatus according to a first embodiment of the present invention.

Next, the functional configuration of the ophthalmological apparatus 10 according to the first embodiment will be described with reference to FIG. 1. FIG. 1 is a block diagram illustrating the functional configuration of the ophthalmological apparatus 10. The ophthalmological apparatus 10 includes an image acquisition unit 110, a storage unit 120, an image processing unit 130, and an instruction acquisition unit 140.

Also, the image processing unit 130 includes a decision unit 131, an alignment unit 132, and a display unit 133. The decision unit 131 includes a determination unit 1311, a magnification decision unit 1312, a position decision unit 1313, and an order decision unit 1314.

The configuration of the SLO image capturing apparatus 20 including an adaptive optics system will be described with reference to FIG. 3.

The SLO image capturing apparatus 20 includes a light source 201. As the light source 201, a super luminescent diode (SLD) light source is used, for example. In the first embodiment, a single light source is used for image capturing and wavefront measurement; however, separate light sources may be used and light emitted from the respective light sources may be combined later.

Light radiated from the light source 201 propagates through a single-mode optical fiber 202, and is radiated as measurement light 205 of parallel rays by a collimator 203.

The radiated measurement light 205 passes through an optical splitter 204, which includes a beam splitter, and is led to an adaptive optics system.

The adaptive optics system includes an optical splitter 206, a wavefront sensor 215, a wavefront correction device 208, and reflection mirrors 207-1 to 207-4 for leading light. Note that the reflection mirrors 207-1 to 207-4 are arranged such that at least the pupil of the eye and the wavefront sensor 215 or the wavefront correction device 208 are optically conjugate. Also, in the first embodiment, a beam splitter is used as the optical splitter 206. In the first embodiment, a spatial phase modulator using a liquid crystal element is used as the wavefront correction device 208. Alternatively, a deformable mirror may be used as the wavefront correction device 208.

The light having passed through the adaptive optics system is used for one-dimensional or two-dimensional scanning by a scanning optical system 209.

In the first embodiment, two galvano scanners are used as the scanning optical system 209 for main scanning (in a direction horizontal to the fundus) and for sub scanning (in a direction vertical to the fundus). Alternatively, a resonance scanner may be used for the main scanning side of the scanning optical system 209 in order to speed up image capturing.

The measurement light 205 used in scanning by the scanning optical system 209 is radiated to an eye 211 through eyepiece lenses 210-1 and 210-2. The measurement light 205 radiated to the eye 211 is reflected or scattered by the fundus. By adjusting the positions of the eyepiece lenses 210-1 and 210-2, optimum radiation can be performed in accordance with the visibility of the eye 211. In this example, lenses are used as eyepiece components; however, spherical mirrors, for example, may be used.

The light (returning light) reflected or scattered by the retina of the eye 211 propagates through the same path as the incident path in the opposite direction. The returning light is partially reflected by the optical splitter 206 toward the wavefront sensor 215 and is used for measurement of the wavefront of the light beam.

The wavefront sensor 215 is connected to an adaptive optics control unit 216, and delivers the received wavefront to the adaptive optics control unit 216. The wavefront correction device 208 is also connected to the adaptive optics control unit 216, and performs modulation based on an instruction received from the adaptive optics control unit 216. The adaptive optics control unit 216 calculates, on the basis of the wavefront obtained based on the measurement result obtained by the wavefront sensor 215, a modulation amount (correction amount) with which the wavefront is corrected to an aberration-free wavefront, and instructs the wavefront correction device 208 to perform such modulation. Note that measurement of the wavefront and instruction to the wavefront correction device 208 are repeatedly performed. In this way, feedback control is performed so as to obtain an optimum wavefront.

The light having passed the optical splitter 206 is partially reflected by the optical splitter 204 to be led to a light intensity sensor 214 through a collimator 212 and an optical fiber 213. The light intensity sensor 214 converts the light into an electric signal. The electric signal is constructed into an eye image by a control unit 217, and the resulting eye image is displayed on a display 218.

Figure 3:
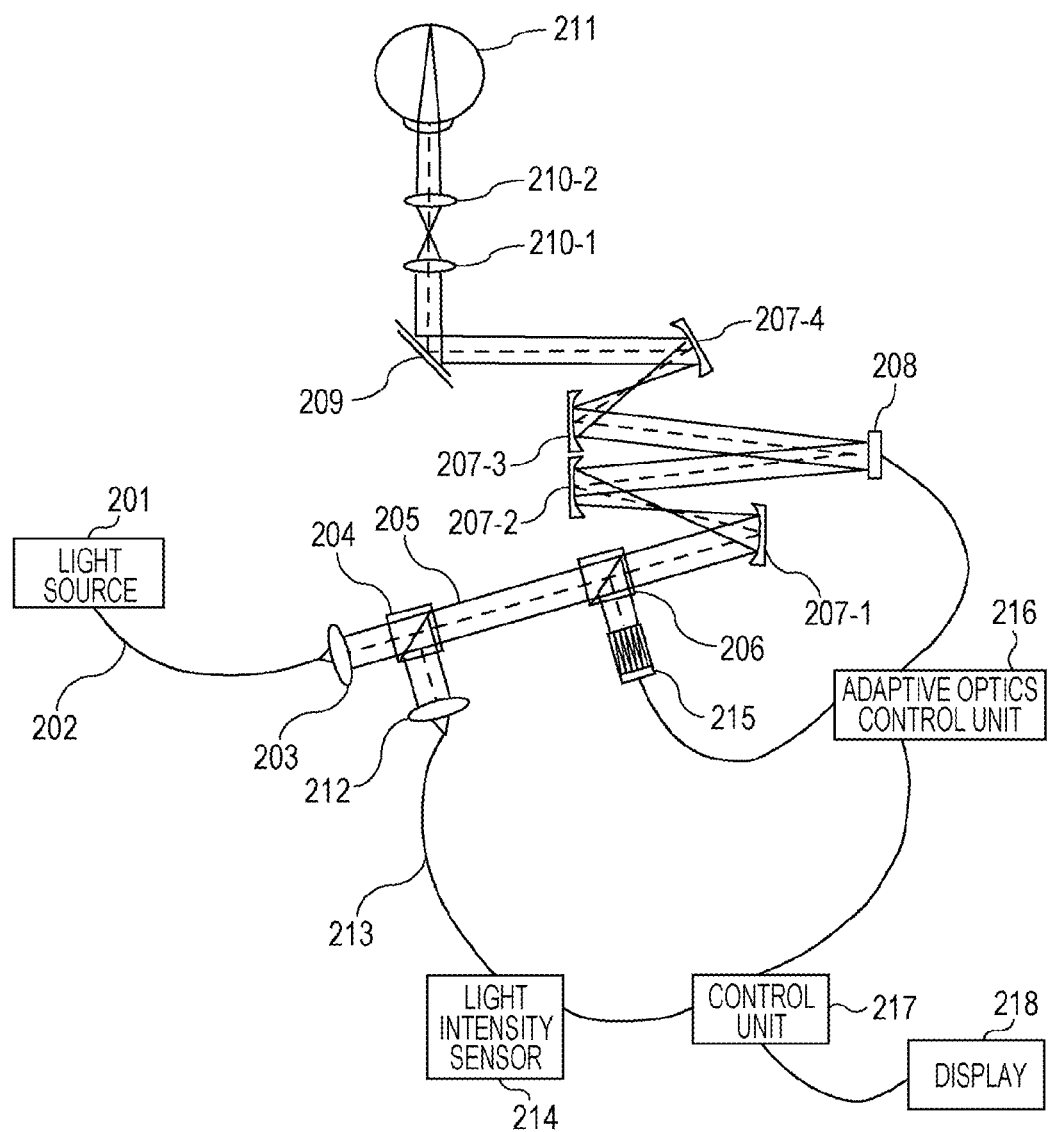
FIG. 3 is a diagram illustrating an example of the configuration of an SLO image capturing apparatus according to the first embodiment of the present invention.

By increasing the swinging angle of the scanning optical system 209 and instructing the adaptive optics control unit 216 not to perform aberration correction in the configuration illustrated in FIG. 3, the SLO image capturing apparatus 20 can operate as an ordinary SLO apparatus and capture a wide-angle SLO image (low-magnification image Dl).

Figure 4:
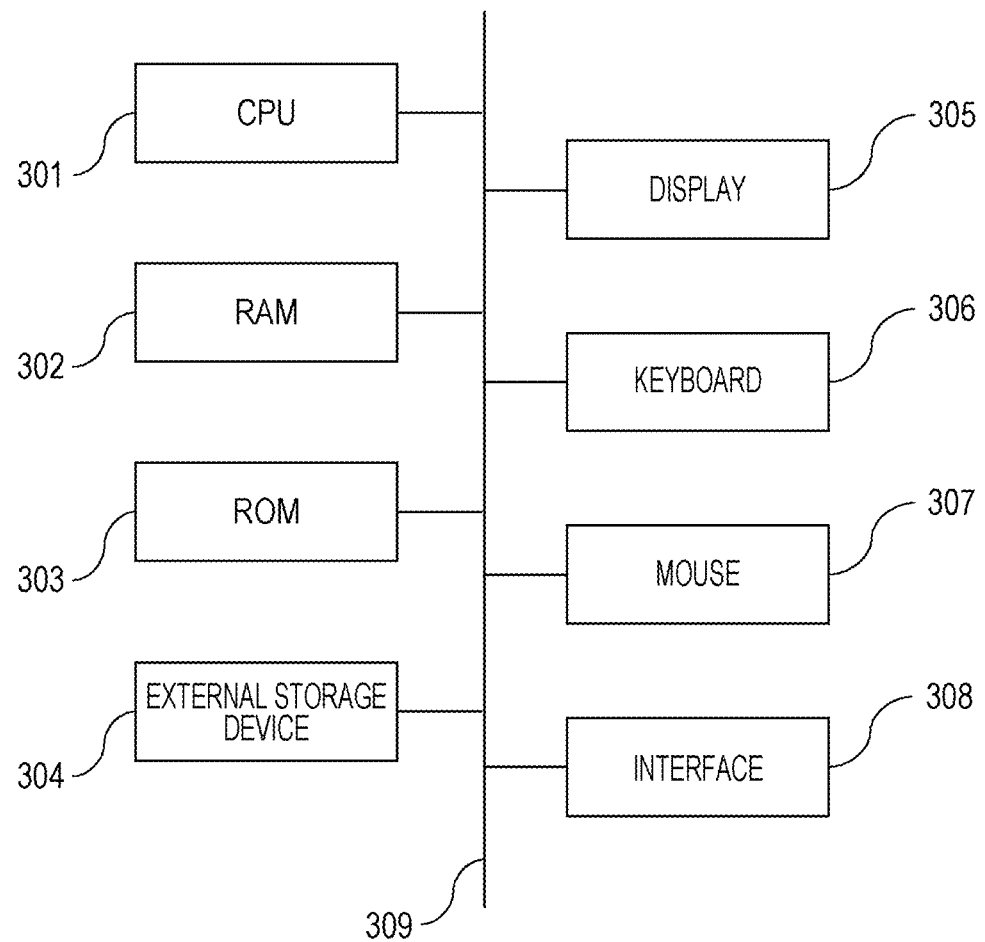
FIG. 4 is a block diagram illustrating an example of the hardware configuration of a computer that includes hardware corresponding to a storage unit and an image processing unit and that stores and executes software implementing other units.

Next, the hardware configuration of the ophthalmological apparatus 10 will be described with reference to FIG. 4. Referring to FIG. 4, the ophthalmological apparatus 10 includes a central processing unit (CPU) 301, a random access memory (RAM) 302, a read only memory (ROM) 303, an external storage device 304, a display 305, a keyboard 306, a mouse 307, and an interface 308. The external storage device 304 stores a control program implementing image processing functions according to the first embodiment and data used during execution of the control program. These control program and data are loaded into the RAM 302 via a bus 309 as needed, under control of the CPU 301. The loaded program is executed by the CPU 301 so as to implement the functional units described below.

Figure 5:
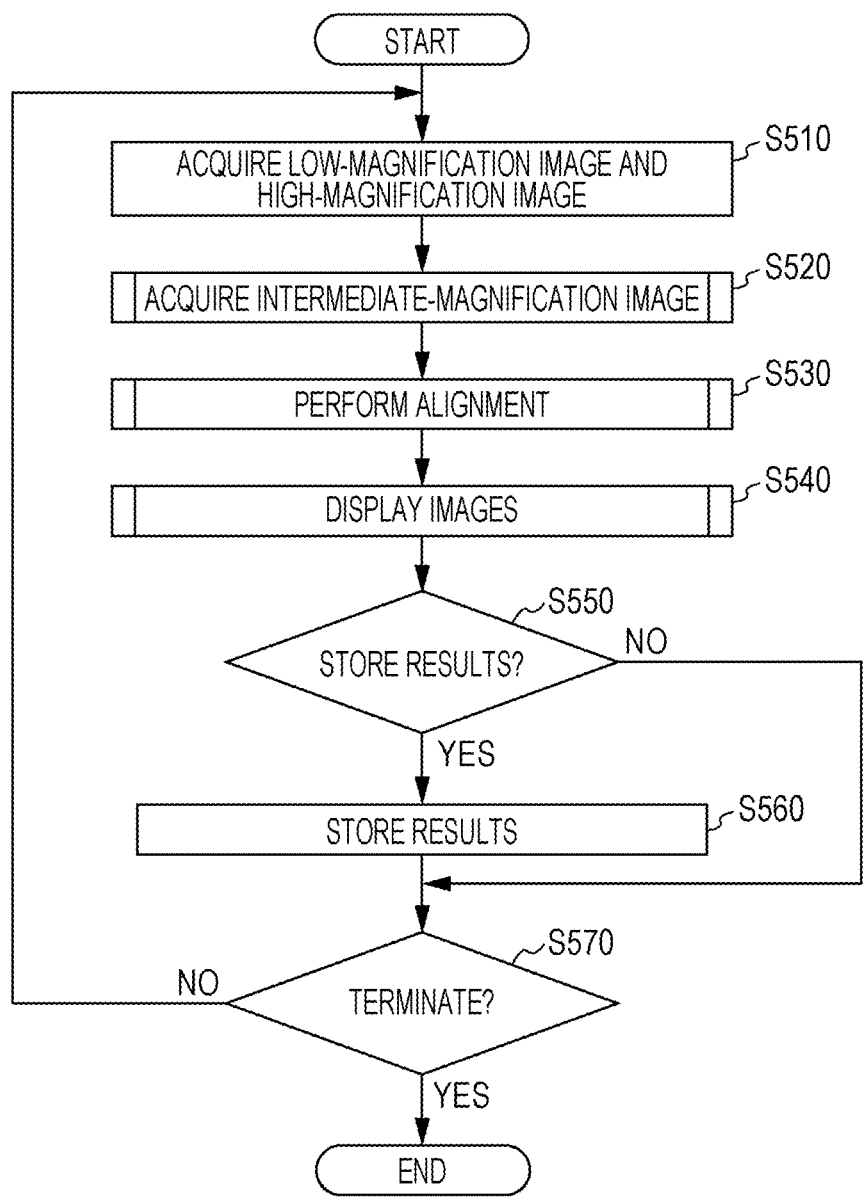
FIG. 5 is a flowchart illustrating an example of a process performed by the ophthalmological apparatus according to the first embodiment of the present invention.

Functional units included in the ophthalmological apparatus 10 will be described in relation to a specific procedure executed by the ophthalmological apparatus 10 as illustrated in a flowchart of FIG. 5.

Step S510

The image acquisition unit 110 requests the SLO image capturing apparatus 20 to acquire the low-magnification image Dl and the high-magnification unit Dh and the fixation positions Fl and Fh. In the first embodiment, the low-magnification image Dl is captured with the fixation position Fl being set at the fovea of the macula area and the high-magnification image Dh is captured with the fixation position Fh being set at the parafovea. That is, the image acquisition unit 110 corresponds to an example of an image acquisition unit configured to acquire images of different magnifications. Note that the image capture position setting method is not limited to this one, and the image capture positions may be set to any given positions.

In response to the request, the SLO image capturing unit 20 captures the low-magnification image Dl and the high-magnification image Dh, and transmits the low-magnification image Dl and the high-magnification image Dh and the fixation positions Fl and Fh. Accordingly, the image acquisition unit 110 receives the low-magnification image Dl, the high-magnification image Dh, and the fixation positions Fl and Fh from the SLO image capturing apparatus 20 via the LAN 30. The image acquisition unit 110 stores the received low-magnification image Dl, high-magnification image Dh, and fixation positions Fl and Fh in the storage unit 120.

Step S520

The decision unit 131 determines whether the intermediate-magnification image Dm needs to be acquired, which has an intermediate resolution between a resolution of the low-magnification image Dl and a resolution of the high-magnification image Dh. If the decision unit 131 determines that the intermediate-magnification image Dm needs to be acquired, the decision unit 131 decides a capture magnification at which, a capture position at which, and an order in which the intermediate-magnification image Dm is to be captured. Also, the decision unit 131 requests the image acquisition unit 110 to acquire the intermediate-magnification image Dm. In response to this request, the image acquisition unit 110 acquires the intermediate-magnification image Dm. Here, the decision unit 131 corresponds to an example of a decision unit configured to decide, based on at least the images acquired by the image acquisition unit or capture conditions of the acquired images, a method for capturing an image of an intermediate magnification that is between the magnifications of the images acquired by the image acquisition unit.

The intermediate-magnification image Dm is acquired using two methods: 1) the image acquisition unit 110 requests the SLO image capturing apparatus 20 to capture the intermediate-magnification image Dm, and the SLO image capturing apparatus 20 transfers the captured intermediate-magnification image Dm to the storage unit 120; and 2) the image acquisition unit 110 requests the data server 40 to transfer the intermediate-magnification image Dm stored in the data server 40, and the data server 40 transfers the intermediate-magnification image Dm. In the first embodiment, the case of using the method 1) will be described.

Note that the present invention is not limited to the case of using the method 1) and may be carried out using the method 2).

Figure 7:
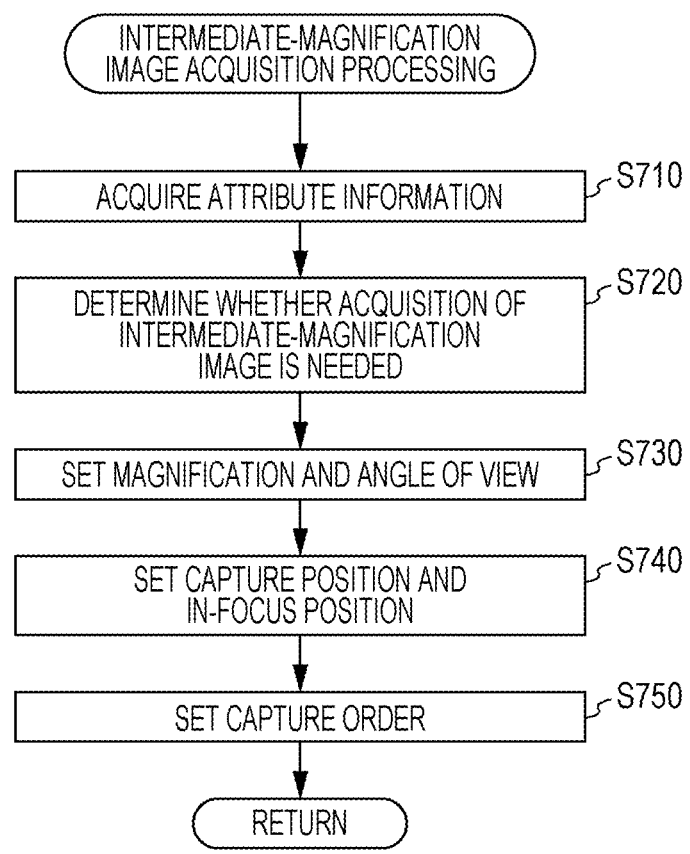
FIG. 7 is a flowchart illustrating an example of details of processing performed in step S520 in the first embodiment of the present invention.

Processing performed in step S520 will be described in detail later with reference to a flowchart illustrated in FIG. 7.

Step S530

The alignment unit 132 performs alignment of the low-magnification image Dl and the high-magnification image Dh. In the case where the intermediate-magnification image Dm has been acquired, the position of the high-magnification image Dh on the low-magnification image Dl is decided using the intermediate-magnification image Dm in step S530. Here, the alignment unit 132 corresponds to an example of an alignment unit configured to align the acquired images.

Figure 9:
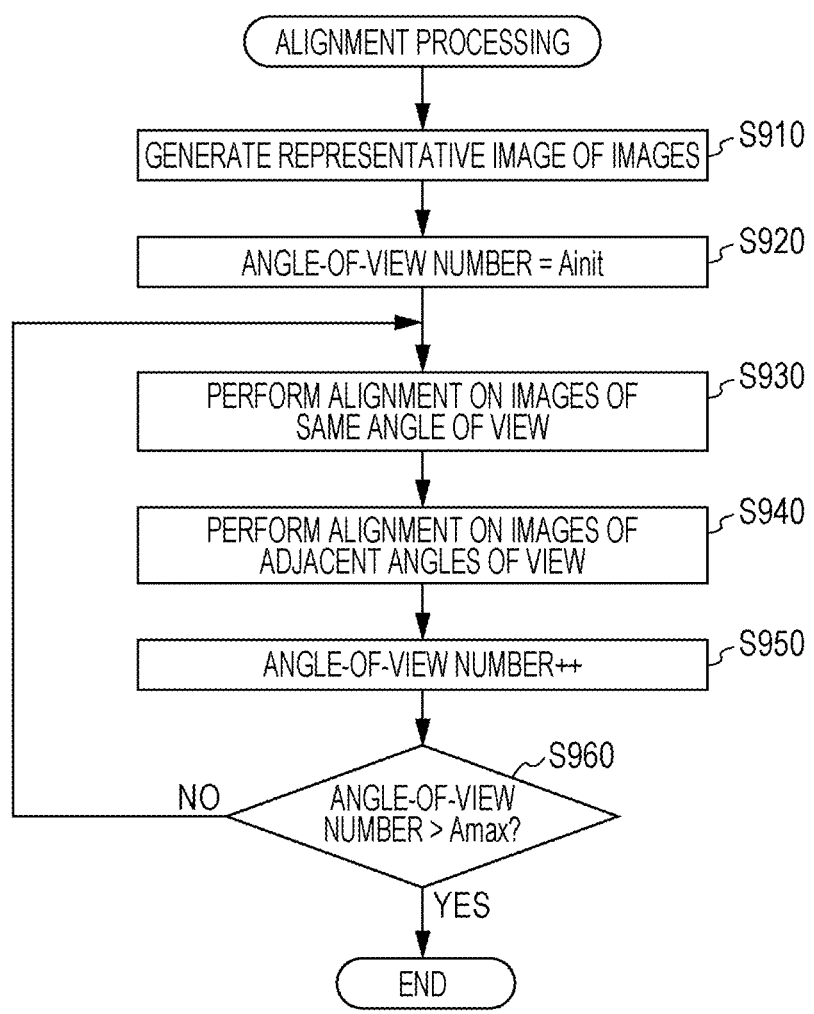
FIG. 9 is a flowchart illustrating an example of details of processing performed in step S530 in the first embodiment of the present invention.

Processing performed in step S530 will be described in detail later with reference to a flowchart illustrated in FIG. 9.

Step S540

The display unit 133, which corresponds to an example of a display unit, superimposes the high-magnification image Dh on the low-magnification image Dl, on the basis of a value of an alignment parameter obtained in step S530.

In the first embodiment, information of a scanning position of an eye tomographic image is superimposed on the low-magnification image Dl. Thus, the information of the scanning position of the eye tomographic image can be superimposed on the high-magnification image Dh.

Figure 10:
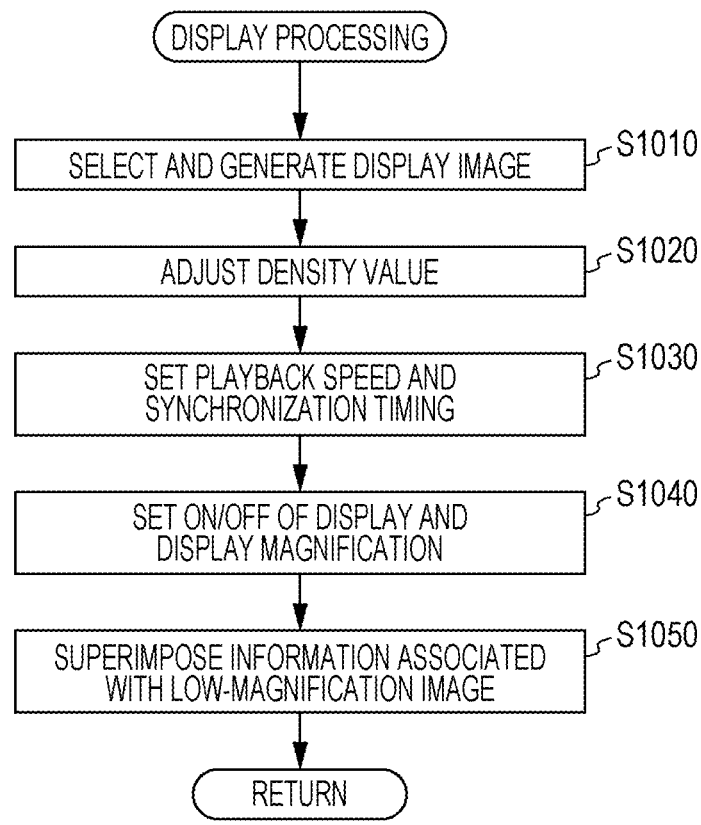
FIG. 10 is a flowchart illustrating an example of details of processing performed in step S540 in the first embodiment of the present invention.

Processing performed in step S540 will be described in detail later with reference to a flowchart illustrated in FIG. 10.

Figure 15:
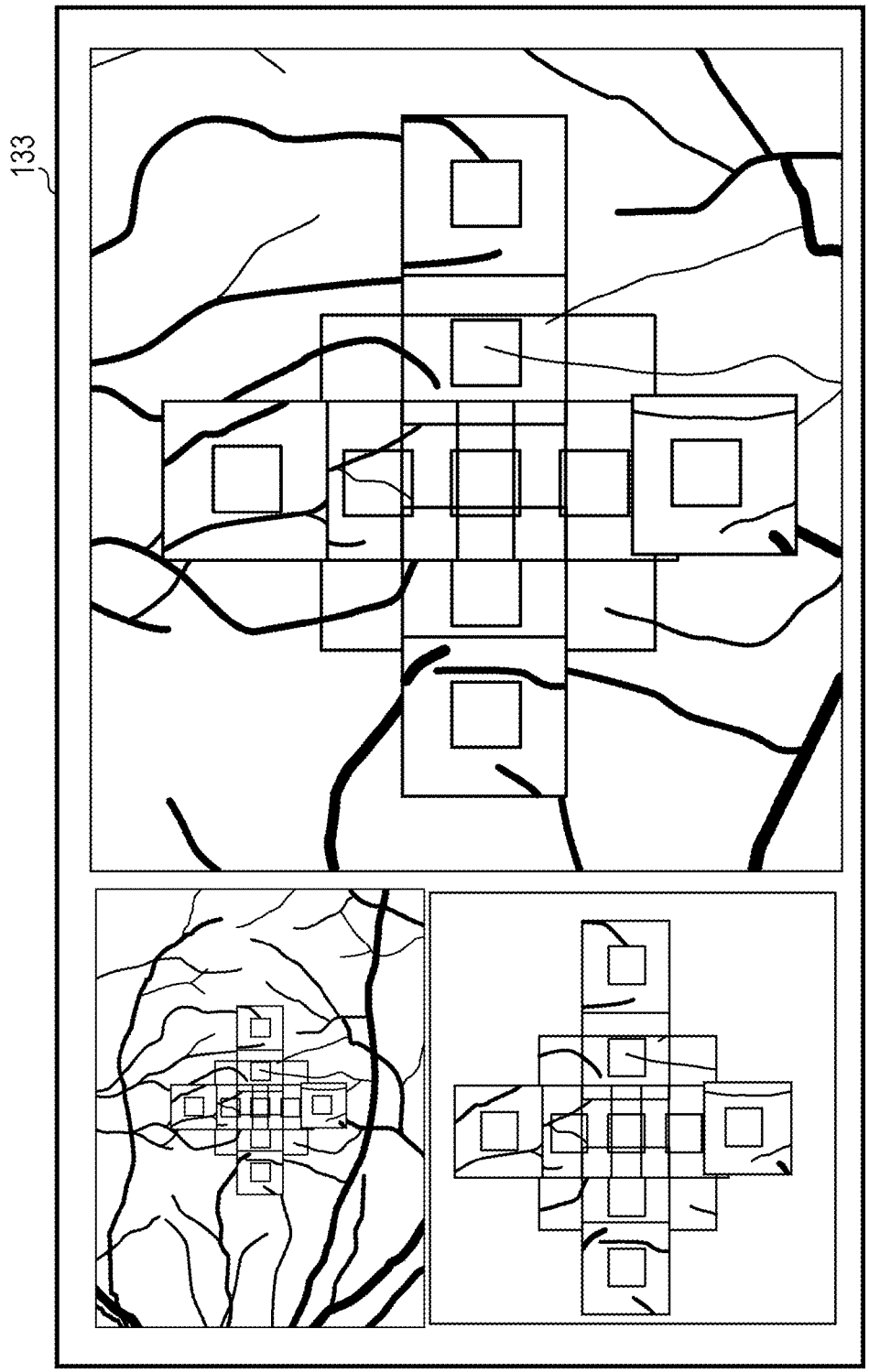
FIG. 15 is a diagram illustrating an example of a displayed screen image.

The display unit 133 may display an image obtained by superimposing the low-magnification image Dl, the intermediate-magnification image Dm, and the high-magnification image Dh; an enlarged image of the image obtained by superimposition; and an image obtained by superimposing the intermediate-magnification image Dm and the high-magnification image Dh. Specifically, the display unit 133 may display an image such as the one illustrated in FIG. 15. Referring to FIG. 15, three images of different magnifications are superimposed on the low-magnification image Dl. In the first embodiment, the number of images superimposed is not limited to three as illustrated in FIG. 15 and may be four or more.

Figure 16:
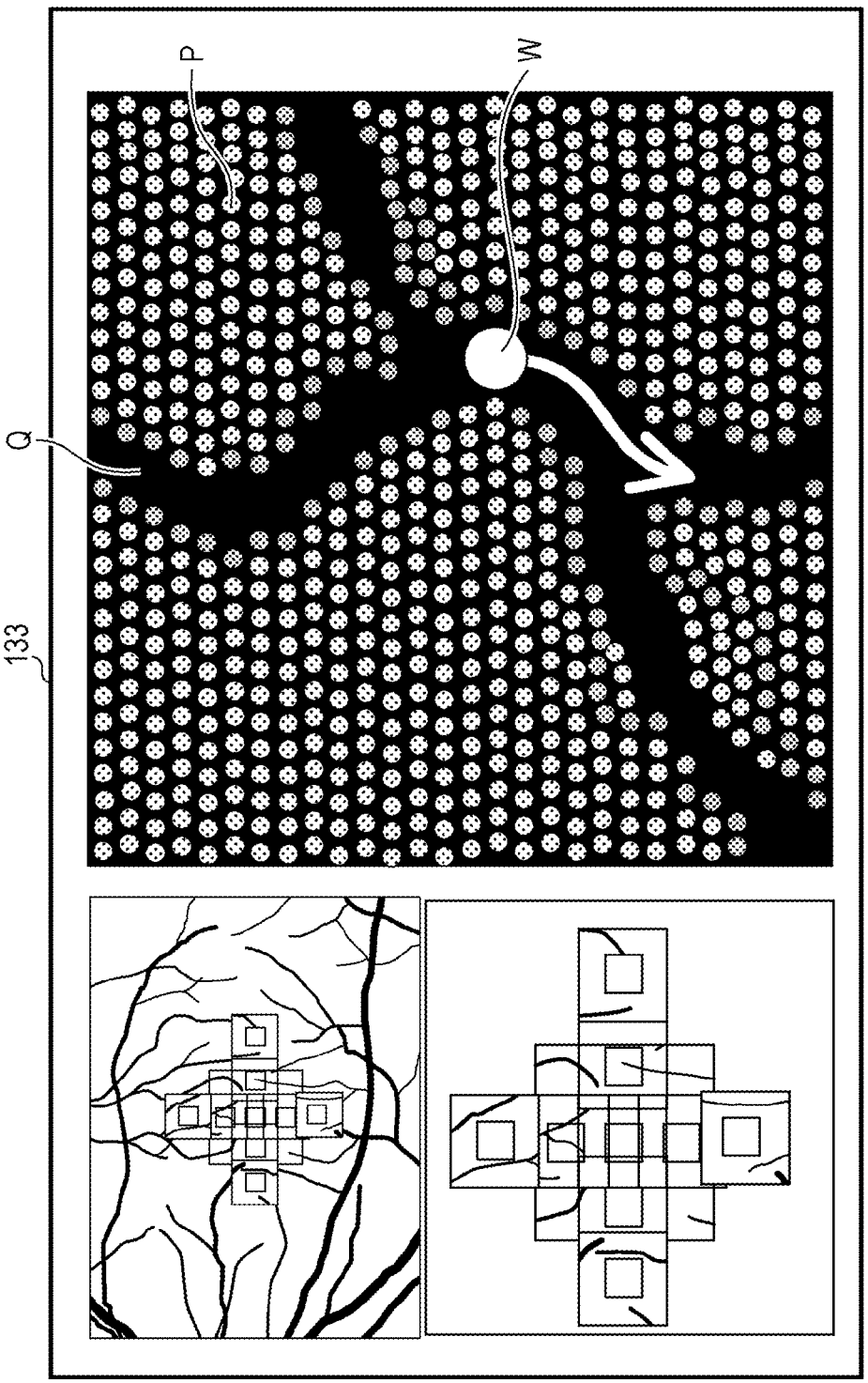
FIG. 16 is a diagram illustrating an example of a displayed screen image.

Alternatively, the display unit 133 may display an image obtained by superimposing the low-magnification image Dl, the intermediate-magnification image Dm, and the high-magnification image Dh; an image obtained by superimposing the intermediate-magnification image Dm and the high-magnification image Dh; and the high-magnification image Dh specified by a user. Specifically, the display unit 133 may display an image such as the one illustrated in FIG. 16. Referring to FIG. 16, three images of different magnifications are superimposed on the low-magnification image Dl.

In this case, the high-magnification image Dh may be an image obtained by superimposing a plurality of images or may be a moving image. A plurality of images may be arranged on the display unit 133 in a given manner. Also, the high-magnification image Dh may be displayed as a moving image or a still image in a switchable manner.

Figure 17:
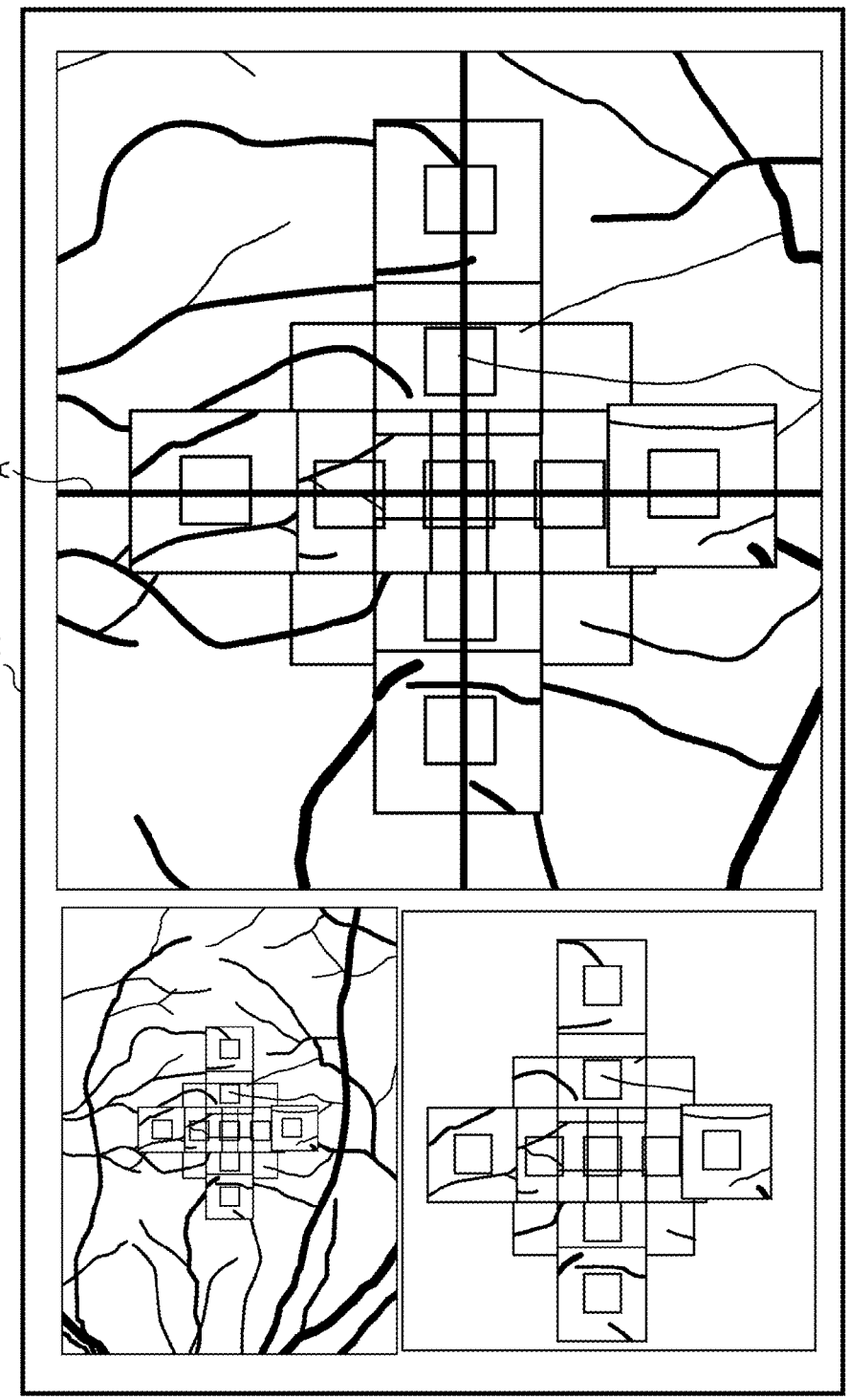
FIG. 17 is a diagram illustrating an example of a displayed screen image.

Because the high-magnification image Dh can be displayed on the low-magnification image Dl on which the capture position of a tomographic image can be displayed, the capture position of the tomographic image can also be displayed on the high-magnification image Dh. For example, a capture position A of a tomographic image can be displayed on the high-magnification image Dh as illustrated in FIG. 17.

Step S550

The instruction acquisition unit 140 acquires, from outside, an instruction as to whether to store the low-magnification image Dl, the intermediate-magnification image Dm, and the high-magnification image Dh, the fixation positions Fl, Fm, and Fh, and the value of the alignment parameter obtained in step S530 in the data server 40. This instruction is input by an operator via the keyboard 306 or the mouse 307, for example. If an instruction to store is input, the process proceeds to step S560. If not, the process proceeds to step S570.

Step S560

The image processing unit 130 transmits, to the data server 40, the examination date and time; information identifying a subject's eye; the low-magnification image Dl, the intermediate-magnification image Dm, and the high-magnification image Dh; features of the eye; the fixation positions Fl, Fm, and Fh; and the value of the alignment parameter in association with one another.

Step S570

The instruction acquisition unit 140 acquires, from outside, an instruction as to whether to terminate the process performed by the ophthalmological apparatus 10 for the low-magnification image Dl and the high-magnification image Dh. This instruction is input by an operator via the keyboard 306 or the mouse 307, for example. If an instruction to terminate the process is acquired, the process for the low-magnification image Dl and the high-magnification image Dh ends. If an instruction to continue the process is acquired, the process returns to step S510 and the process is performed for the next subject's eye (or the same subject's eye again).

Referring next to the flowchart illustrated in FIG. 7, the processing performed in step S520 will be described in detail.

Conditions related to capturing of the intermediate-magnification image Dm having an intermediate magnification between the magnification of the low-magnification image Dl and the magnification of the high-magnification image Dh include a condition as to whether the intermediate-magnification image Dm needs to be acquired, a capture magnification (angle of view and pixel size), a capture position, an in-focus position, and a capture order. Note that the capture order is decided only when a plurality of intermediate-magnification images Dm are acquired.

Values of these capture conditions may be set using two methods, that is, a) by fixing the capture magnification or selecting the capture magnification from options and by making the capture position settable to a given position; and b) by making the capture magnification settable to a given value and setting the capture position to be the same as that of the high-magnification image Dh.

The method a) is advantageous in that a possible value of each attribute of the acquired intermediate-magnification image Dm can be limited; however, the method a) involves redo of aberration correction in the case where the capture position of the intermediate-magnification image Dm differs from capture positions of images of other magnifications. In contrast, the method b) does not involve redo of aberration correction to capture the intermediate-magnification image Dm because the capture position is fixed; however, the method b) involves the use of image-capturing-apparatus control software or image management software because the attribute value of the acquired intermediate-magnification image Dm may vary widely.

In the first embodiment, the SLO image capturing apparatus 20 performs aberration correction in real time. Accordingly, the method a) is used. In this case, whether the intermediate-magnification image Dm needs to be acquired and the capture position and in-focus position of the intermediate-magnification image Dm are automatically selected on the basis of settings of the capture magnification (angle of view and pixel size), capture position, and in-focus position of the high-magnification image Dh selected by an operator.

The method for capturing the intermediate-magnification image Dm may be decided using the method b). When the method b) is used, whether the intermediate-magnification image Dm needs to be acquired and the capture magnification (angle of view and pixel size) and in-focus position of the intermediate-magnification image Dm are automatically selected on the basis of settings of the capture magnification (angle of view and pixel size), capture position, and in-focus position of the high-magnification image Dh selected by an operator.

When the method for capturing the intermediate-magnification image Dm is decided, information such as i) a list containing, for each capture magnification (pixel size and angle of view), an image feature frequently observed in the eye in general, ii) a map indicating a probability of existence of a large image feature usable for alignment, iii) a result obtained by extracting features from the low-magnification image Dl and the high-magnification image Dh, and iv) an image quality index value (S/N ratio or average luminance) of the low-magnification image Dl and the high-magnification image Dh may be used.

The information i) is used to determine whether the intermediate-magnification image Dm needs to be acquired and to set the capture magnification.

Figure 6A:
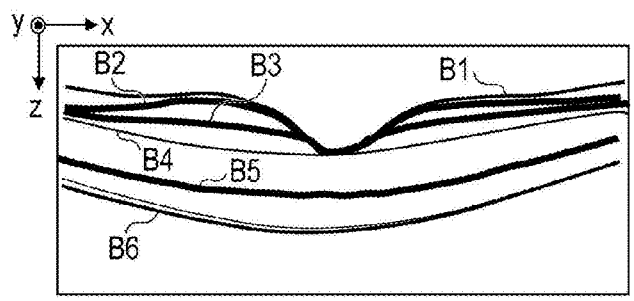
FIGS. 6A to 6H are diagrams illustrating examples of image processing in embodiments of the present invention.
Figure 6B:
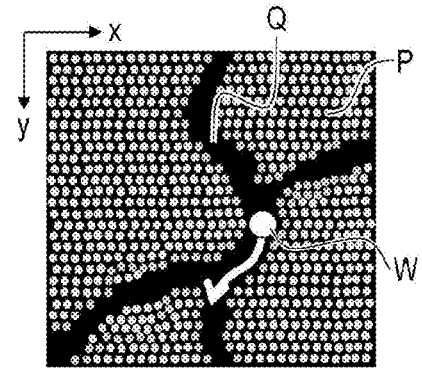
Figure 6C:
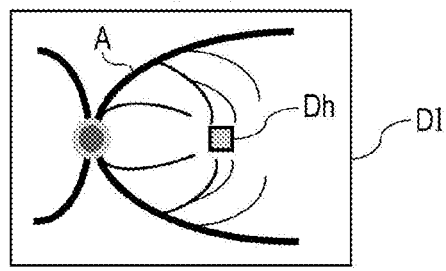
Figure 6D:
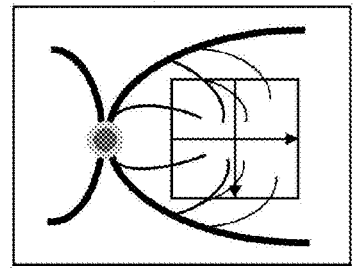
Figure 8A:
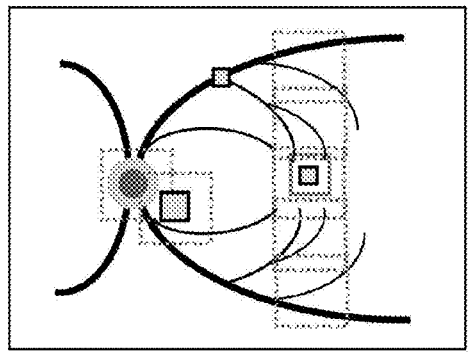
FIGS. 8A to 8H are diagrams illustrating examples of image processing performed in step S520 and S530 in the first embodiment of the present invention.
Figure 8B:
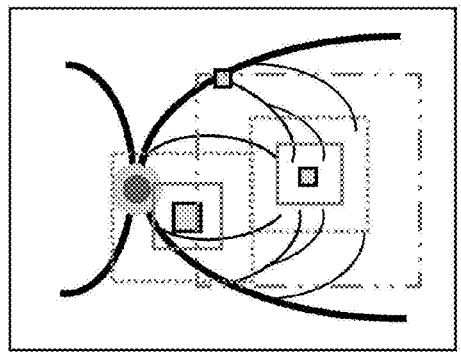
Figure 8C:
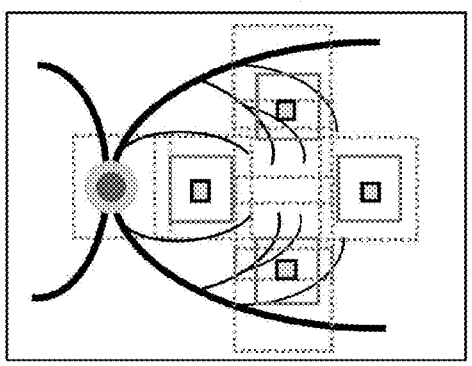

The information ii) is a map that displays, as a probability, locations of landmarks in the eye, such as the optic disc or a vascular arcade (retinal blood vessels surrounding the high-magnification image Dh in a U-shape in FIG. 6C), the locations being obtained from many healthy subjects. The information ii) can be used to determine whether the intermediate-magnification image Dm needs to be acquired and to set the capture magnification and the capture position. FIG. 8E illustrates an example of the existence probability map for the right eye and FIG. 8F illustrates an example of the existence probability map for the left eye.

The information iii) can be used to determine whether the intermediate-magnification image Dm needs to be acquired and to set the capture magnification and the capture position.

The information iv) may be used along with the information i) or ii) in a supplementary manner. For example, in the case where the image quality index value is smaller than a threshold Tq, it is forcibly determined that the intermediate-magnification image Dm needs to be acquired, all selectable intermediate magnifications are forcibly selected, or a space between the capture positions is forcibly set to be small. In the first embodiment, among the conditions used for capturing the intermediate-magnification image Dm, whether the intermediate-magnification image Dm needs to be acquired and the capture magnification are decided using the information i) and the capture position is decided using the information ii). Note that the case of using the information iii) will be described in second and third embodiments.

Step S710

The decision unit 131 acquires attribute information of the low-magnification image Dl and the high-magnification image Dh from the storage unit 120. Specifically, the decision unit 131 acquires information, such as the angle of view [μm], the pixel size [μm/pixel], the fixation position, the in-focus position, the frame rate [frames/sec], the number of frames [frames], and the acquisition date and time.

In the first embodiment, the low-magnification image Dl has attribute information, such as an angle of view of 12800×6400 [μm], a pixel size of 16.0×16.0 [μm/pixel], a fixation position indicating the fovea, an in-focus position indicating the retinal outer layer, a frame rate of 16 [frames/sec], the number of frames indicating 16 [frames], and acquisition date and time indicating Nov. 11, 2011 11:11:11. The high-magnification image Dh has attribute information, such as an angle of view of 400×400 [μm], a pixel size of 1.0×1.0 [μm/pixel], a fixation position indicating the fovea, an in-focus position indicating the retinal outer layer, a frame rate of 32 [frames/sec], the number of frames indicating 32 [frames], and acquisition date and time indicating Nov. 11, 2011 11:12:12.

Step S720

The determination unit 1311 determines whether the intermediate-magnification image Dm needs to be acquired. In the first embodiment, the determination unit 1311 makes this determination using the following list which includes, for each capture magnification (specifically, angle of view and pixel size), image features frequently observed in the eye in general.

| Magnification number | Angle of view [μm] | Pixel size [μm/pixel] | Image feature (in-focus: inner layer) | Image feature (in-focus: outer layer) |
| --- | --- | --- | --- | --- |
| 4 | 400 × 400 | 1.0 × 1.0 | Nerve fibers Capillaries | Photoreceptor cells Capillaries |
| 3 | 800 × 800 | 2.0 × 2.0 | Capillaries Thin arteries/veins | Same as on the left |
| 2 | 1600 × 1600 | 4.0 × 4.0 | Thin arteries/veins Vascular arcade | Same as on the left |
| 1 | 12800 × 6400 | 16.0 × 16.0 | Vascular arcade Optic disc | Same as on the left |

Four combinations are selectable based on the magnification (angle of view and pixel size) of a to-be-captured image. The list shows image features often observed in an image of each magnification. In particular, for an image with the highest magnification (the magnification number 4), observable image features change depending on the in-focus position. Thus, the list shows both image features observed when the in-focus position is set to the retinal inner layer and image features observed when the in-focus position is set to the retinal outer layer. For each of images with the magnification numbers 1, 2, and 3, common image features are observed when the in-focus position is set to the inner layer and when the in-focus position is set to the outer layer.

In the first embodiment, the in-focus position is set to the retinal outer layer for both the low-magnification image Dl and the high-magnification image Dh. Thus, image features observed when the in-focus position is set to the retinal outer layer are used.

Note that the unit of the angle of view and the pixel size may be respectively represented as [deg] and [deg/pixel] on the basis of the swinging angle of the scanner or as [μm] and [μm/pixel] based on the healthy subject's optic axial length (24 mm).

In general, for healthy subjects, a photoreceptor cell has a size of approximately 2-3 [μm], a capillary has a size of approximately 8-10 [μm], a thin artery or vein has a size of approximately 20-100 [μm], and a vascular arcade has a size of approximately 100-200 [μm], and the optic disc has a size of approximately 1.5 [mm]

The determination unit 1311 determines that the intermediate-magnification image Dm needs to be acquired if the low-magnification image Dl and the high-magnification image Dh have no common image feature by referring to the image feature list. If there is a common image feature, the determination unit 1311 determines that the intermediate-magnification image Dm need not be acquired. In the first embodiment, there is no common image feature, and thus the determination unit 1311 determines that the intermediate-magnification image Dm needs to be acquired.

Step S730

If it is determined in step S720 that the intermediate-magnification image Dm needs to be acquired, the magnification decision unit 1312 decides a capture magnification (angle of view and pixel size) at which the intermediate-magnification image Dm is to be captured. The capture magnification of the intermediate-magnification image Dm is set in accordance with the following policy.

i) A magnification of an image with the highest magnification among intermediate-magnification images Dm having a common image feature with the low-magnification image Dl is set as a first intermediate magnification. A magnification of an image with the lowest magnification among intermediate-magnification images Dm having a common image feature with the high-magnification image Dh is set as a second intermediate magnification. If the first and second intermediate magnifications are the same, this intermediate magnification is set, and then step S730 is terminated.

ii) In the case where the first and second intermediate magnifications are different, if an image feature observed in common in the corresponding intermediate-magnification images is found in the image feature list, the first and second intermediate magnifications are set, and then step S730 is terminated.

iii) If no common image feature is found in the image feature list during the processing of ii), the low-magnification image Dl, the high-magnification image Dh, the firstintermediate-magnification image, and the second-intermediate-magnification image are respectively replaced with the first-intermediate-magnification image, the second-intermediate-magnification image, a third-intermediate-magnification image, and a fourth-intermediate-magnification image, and then the processing of i) and ii) are performed again.

The above-described intermediate magnification selection operation is repeatedly performed until it is determined that an n-th intermediate-magnification image and an (n+1)-th intermediate-magnification image include a common image feature. If the termination condition is not satisfied even when all the selectable intermediate magnifications are used, the intermediate magnifications that have been obtained up to this point are set, and then this step is terminated. That is, the decision unit 131, which corresponds to an example of a decision unit, decides, on the basis of at least the acquired images or the capture conditions of the acquired images, at least one of whether the image of the intermediate magnification needs to be acquired, a capture magnification, angle of view, pixel size, capture position, in-focus position, and capture order of the image of the intermediate magnification.

In the first embodiment, as the angle of view and pixel size of the first-intermediate-magnification image having a common image feature (vascular arcade) with the low-magnification image Dl (with the magnification number 1 in the image feature list), the angle of view and pixel size associated with the magnification number 2 are respectively selected. Specifically, as the angle of view and pixel size of the first-intermediate-magnification image, an angle of view of 1600×1600 [μm] and a pixel size of 4.0×4.0 [μm/pixel] are respectively selected. Also, as the angle of view and pixel size of the second-intermediate-magnification image having a common image feature (capillaries) with the high-magnification image Dh (with the magnification number 4), the angle of view and pixel size associated with the magnification number 3 are respectively selected. Specifically, as the angle of view and pixel size of the second-intermediate-magnification image, an angle of view of 800×800 [μm] and a pixel size of 2.0×2.0 [μm/pixel] are respectively selected. There is a common image feature for the magnification numbers 2 and 3, and thus these magnifications are set as the intermediate magnifications. Then, the process proceeds to step S740.

Step S740

The position decision unit 1313 sets capture positions and in-focus positions of the intermediate-magnification images Dmj having the magnifications (angles of view and pixel sizes) set in step S730.

In the first embodiment, data of the fixation position, angle of view, and pixel size of the high-magnification image Dh and the existence probability map of a large image feature that is usable for alignment are used to decide the capture positions of the intermediate-magnification images Dmj. The existence probability map is a map that indicates, as illustrated in FIG. 8F, an existence probability (through a color density value) of landmarks, such as the optic disc and a vascular arcade, in the eye, the existence probability being determined by obtaining the locations of the landmarks from many healthy subjects.

Among settings regarding capture positions of the intermediate-magnification images Dmj, a method for setting capture positions of the intermediate-magnification image D2j associated with the magnification number 2 will be described first. Specifically, the value at the capture position of the high-magnification image Dh in the existence probability map is determined. If the existence probability value is less than a certain value (colorless), the intermediate-magnification images D2j are captured by sequentially moving the capture position in a direction for which the number of the intermediate-magnification images D2j to be captured in a range from the capture position of the high-magnification image Dh to a region of the high existence probability (deep color) is smallest. At this time, the capture position is sequentially moved by a certain distance so that the adjacent intermediate-magnification images D2j overlap by a certain amount.

In the first embodiment, because there is no vascular arcade at the capture position (parafovea) of the high-magnification image Dh, the intermediate-magnification images D2j associated with the magnification number 2 are acquired by sequentially moving the fixation position in the vertical direction so that the intermediate-magnification image D2j include the vascular region. At this time, the fixation position is sequentially moved by a certain distance so that the adjacent intermediate-magnification images D2j overlap by a quarter of their widths. A plurality of dotted-line rectangular areas arranged in the vertical direction in FIG. 8A represent the capture positions of the intermediate-magnification images D2j.

The capture position of the intermediate-magnification image D3 corresponding to the magnification number 3 is set to be the same as the capture position of the high-magnification image Dh. This is because the capture positions of the intermediate-magnification images D2j corresponding to the magnification number 2 include the capture position of the high-magnification image Dh.

The in-focus position is set in the following manner. If the in-focus positions of the low-magnification image Dl and the high-magnification image Dh are the same, the in-focus position of the intermediate-magnification images D2j are set to be the same as this in-focus position. If not, the in-focus position is set in the following manner using "i", which denotes the magnification number of the intermediate-magnification image Dmj (is 2 in the first embodiment).

Specifically, the in-focus position of the intermediate-magnification image D2 associated with the magnification number 2 is set to a position which is spaced apart from the in-focus position of the low-magnification image Dl by "(a distance from the in-focus position of the low-magnification image Dl to the in-focus position of the high-magnification image Dh)×1/(i+1)" toward the in-focus position of the high-magnification image Dh. The in-focus position of the intermediate-magnification image D3 associated with the magnification number 3 is set to a position which is spaced apart from the in-focus position of the low-magnification image by "(a distance from the in-focus position of the low-magnification image Dl to the in-focus position of the high-magnification image Dh)×2/(i+1)" toward the in-focus position of the high-magnification image Dh.

Note that the in-focus position setting method is not limited to this one. For example, in the case where the in-focus positions of the low-magnification image Dl and the high-magnification image Dh are different, the in-focus positions of the intermediate-magnification images associated with the magnification numbers 2 and 3 may be set to positions located between the in-focus positions of the low-magnification image Dl and the high-magnification image Dh; or to be the same as the in-focus position of the low-magnification image Dl or the high-magnification image Dh.

Step S750

The order decision unit 1314 decides an order in which the intermediate-magnification images Dmj decided in steps S720 to S740 are to be captured.

In the first embodiment, it is assumed that intermediate-magnification images are captured in ascending order of magnification. In the case where a plurality of intermediate-magnification images of the same magnification are captured, capturing is started from a position including a high existence probability area on the map and is sequentially performed from the closest fixation position. The capture order of the intermediate-magnification images is not limited to this one and may be set using any given setting method.

Referring next to a flowchart illustrated in FIG. 9, the alignment processing performed in step S530 will be described in detail. Note that the term "angle-of-view number" used in the description of the processing performed in step S530 has the same meaning as the magnification number described in step S720. Accordingly, in the first embodiment, Ainit=1 and Amax=4.

Step S910

A representative image is generated from each moving image (the low-magnification image Dl, the intermediate-magnification image Dm, or the high-magnification image Dh) acquired by the image acquisition unit 110. Specifically, at least one of the images of different magnifications is an image generated on the basis of a tomographic image of an eye or a moving image of an eye.

In the first embodiment, a reference image that is set during alignment of frames of the moving image is set as the representative image. Any given available setting method may be used to set the reference frame. In the first embodiment, the first frame is set as the reference frame. The representative image generation method is not limited to this one, and for example, an image may be generated by superimposition for each of the moving images and be set as the representative image.

Any given available method may be used to perform alignment of frames. In the first embodiment, alignment of frames is performed using a correlation coefficient as an image similarity evaluation function and using Affine transformation as a coordinate conversion method.

Step S920

The angle-of-view number is initialized. The initial value Ainit may vary depending on the setting regarding an order of alignment. In the first embodiment, alignment is performed in ascending order of magnification, sequentially from the low-magnification image Dl. That is, the angle-of-view number (1) assigned to the low-magnification image Dl is substituted into the initial value Ainit. Then, the process proceeds to step S930.

Step S930

Figure 8D:
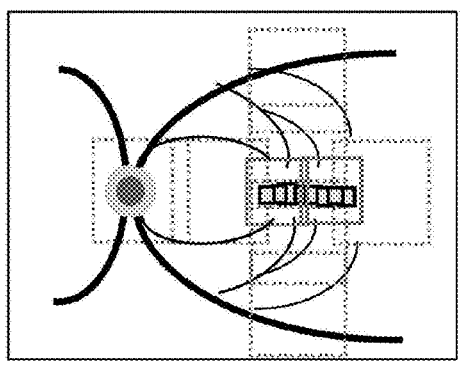
Figure 8E:
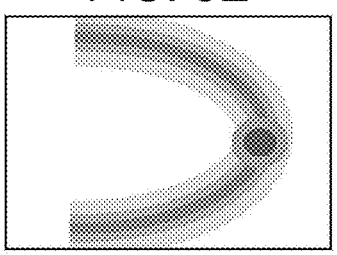
Figure 8F:
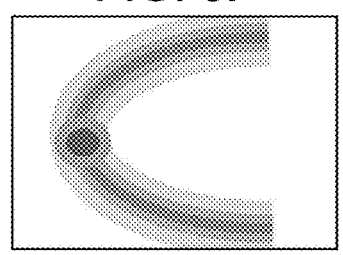

In the case where there are a plurality of images of the same magnification that have an overlapping area (high-magnification images (solid-line rectangular areas) illustrated in FIG. 8D), the alignment unit 132 calculates a similarity between the images in the overlapping area, and the images of the same magnification are aligned to a position where the largest similarly is obtained.

In the first embodiment, a plurality of intermediate-magnification images D2j associated with the magnification number 2 are captured at different positions. Thus, alignment for images of the same magnification is performed on the intermediate-magnification images D2j associated with the magnification number 2. Any given available methods may be used to determine the similarity between images and to convert the coordinates. In the first embodiment, alignment of images of the same angle of view is performed using a correlation coefficient as an image similarity evaluation function and using Affine transformation as the coordinate conversion method.

Step S940

The alignment unit 132 performs alignment of images with adjacent angle-of-view numbers.

Specifically, the alignment unit 132 performs alignment of images with the angle-of-view numbers A and A-1. Note that this step is omitted when the angle-of-view number is the initial value Ainit.

Alignment is performed sequentially from the image with the lowest magnification. Accordingly, alignment is performed sequentially from the image with the smallest angle-of-view number (the smallest magnification number).

In the case where there are a plurality of images of the same magnification that have been aligned in step S930, alignment is performed by treating the plurality of images of the same magnification as one image.

In the case where there are a plurality of images of the same magnification that are independent of one another (whose capture positions are spaced apart and which do not have any overlapping area) (high-magnification images (solid-line rectangular areas) illustrated in FIG. 8C), alignment is performed as many times as the number of the independent images. Note that in the case where there are a plurality of independent images of the same magnification for each of the plurality of magnifications, alignment is repeatedly performed for each adjacent magnification pair and then for each fixation position (in the case where magnification is prioritized). Alternatively, alignment may be performed for a certain adjacent magnification pair and for each fixation position, and then for anther adjacent magnification pair (in the case where the fixation position is prioritized).

Note that the use of the fixation position of the image as the initial value of the alignment parameter related to translation (x and y) may decrease the variation range of the alignment parameter.

For example, in the case where the image quality (such as the S/N ratio) is significantly low and thus the similarity between images does not exceed a threshold Tr even if the alignment parameter is varied, the images may be aligned to the fixation position by considering there is no correct solution of the alignment parameter.

Step S950

The angle-of-view number is increased by 1. The process then proceeds to step S960.

Step S960

A determination is made as to whether the angle-of-view number exceeds the maximum value Amax. If the angle-of-view number is greater than the maximum value Amax, the process proceeds to step S540. If not, the process returns to step S930.

Referring next to a flowchart illustrated in FIG. 10, the processing performed in step S540 will be described in detail.

Step S1010

The display unit 133 selects a to-be-displayed frame of the high-magnification image Dh.

In step S910, a representative frame suitable for alignment has been generated. If this representative frame is the same as a representative to-be-displayed frame generated/selected in step S1010, processing of this step may be omitted.

In step S1010, a frame including an observation-target or measurement-target cell or lesion or an eye-blinking-free or fixation-disparity-free frame is selected. The former is set by an operator making specification via the instruction acquisition unit 140. The latter is set by selecting the first frame from among frames that satisfy a condition that the average luminance of the entire frame is higher than or equal to a threshold T1 and a condition that a change in the alignment parameter between frames is less than a threshold T2. Note that the method used to determine eye blinking and fixation disparity is not limited to the above-described one, and any available method may be used.

Step S1020

In the case where a plurality of high-magnification images Dhk are acquired, the display unit 133 corrects a difference in color density between the high-magnification images Dhk. Any available luminance correction method may be used. In the first embodiment, the difference in color density is corrected by generating histograms Hk for the high-magnification images Dhk and performing linear transformation on luminance values of the high-magnification images Dhk so that averages and variances of the histograms Hk are common to the high-magnification images Dhk.

Step S1030

In the case where the high-magnification image Dh is displayed as a moving image on the low-magnification image Dl, the display unit 133 sets a playback speed of the high-magnification image Dh. A playback speed adjustment slider or a fast-forward button is provided in an image display area. The playback speed is adjusted as a result of an operator making specification via the instruction acquisition unit 140.

Note that in the case where the plurality of high-magnification images Dhk are displayed on the low-magnification image Dl, cycle data based on a biological signal, such as a pulse wave, is acquired at the time of image capturing. Playback timings of the high-magnification images Dhk are synchronized with each other using the cycle data.

Step S1040

The display unit 133 makes a setting of display or non-display of each high-magnification image Dh and a setting of a display magnification of each high-magnification image Dh.

A setting of display or non-display of an image is made in the following manner. A list of the acquired images is displayed on the display 305 and a user interface (hereinafter abbreviated as UI, a checkbox in the first embodiment) is provided near each of the names of the listed acquired images so as to allow an operator to specify ON or OFF with the UI (checkbox) via the instruction acquisition unit 140. A UI (checkbox) used to collectively specify all images and a UI (checkbox) used to collectively specify images of each type are also provided so as to make it easier to switch between display and non-display of many images.

In addition to display or non-display of images, a superimposition order (an order of displayed layers) is set in the case where the high-magnification images Dhk have overlapping areas because their capture positions are close or where multiple images are captured for the same fixation position in step S1040. Any given method including manual setting may be used to set the superimposition order of moving images. In the first embodiment, the image quality index and the amount of fixation disparity are calculated for each image. The linear sum of the image quality index and the amount of fixation disparity is used as an evaluation function. An image with the highest evaluation value is set and displayed as the foremost layer. Any given available index may be used as the image quality index. In the first embodiment, the average luminance of the image histogram is used. As the amount of fixation disparity, a value obtained by summing absolute values of translation distances between adjacent frames of all frames is used. Note that any given index which permits evaluation of fixation disparity may be used.

The display magnification is set as a result of an operator specifying a magnification via the instruction acquisition unit 140.

Step S1050

Figure 6E:
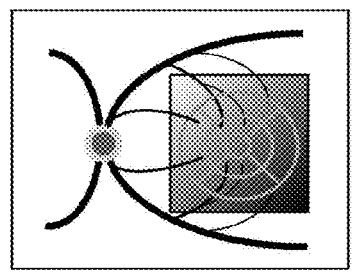
Figure 6F:
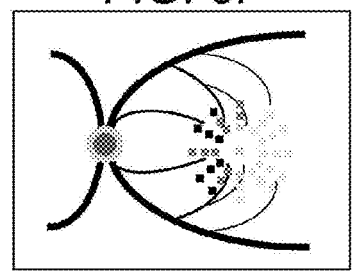
Figure 6G:
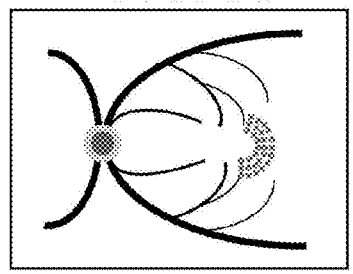
Figure 6H:
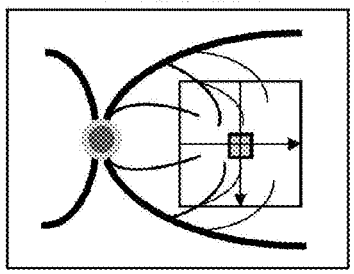

The display unit 133 superimposes scanning position information (scanning line or scanning range) of an eye tomographic image associated with the low-magnification image Dl on the high-magnification image Dh. In the first embodiment, as illustrated in FIG. 6H, a scanning position of a B-scan image obtained by performing cross scanning and a scanning range of a three-dimensional tomographic image obtained by scanning a rectangular area are superimposed on the low-magnification image Dl. Thus, the scanning position of the B-scan image is superimposed on the high-magnification image Dh.

For example, by displaying the high-magnification image Dh of a cell distribution near the scanning position of the eye tomographic image along with the tomographic image obtained at the scanning position, the operator can compare and observe a correspondence between the microscopic cell distribution and the macroscopic layer shape included in the tomographic image.

Note that the display unit 133 permits the operator to adjust transparency of the high-magnification image Dh or low-magnification image Dl via the instruction acquisition unit 140 so as to make it easier to observe the correspondence between the scanning position and the high-magnification image Dh. That is, the instruction acquisition unit 140 corresponds to an example of a control unit configured to control, in a case where images displayed on a lower-magnification image among the images have an overlap, at least one of an order in which the images are superimposed, whether to display the images, and transparencies of the images.

In the first embodiment, the scanning position of the eye tomographic image is used as information superimposed on the high-magnification image Dh; however, the information superimposed is not limited to this information. For example, as illustrated in FIG. 6F, a map of retina sensitivity values may be superimposed on the high-magnification image Dh. Alternatively, as illustrated in FIG. 6E, a map of fundus shape measurement values may be superimposed on the high-magnification image Dh. Alternatively, as illustrated in FIG. 6G, a map of a position irradiated with a therapeutic laser beam may be superimposed on the high-magnification image Dh. In this case, the high-magnification image Dh may be displayed as a moving image, which enables observation of a relationship between the site irradiated with the laser beam and movement of blood cells or a change in shape of blood vessels. Further, a plurality of pieces of information among the above-described maps may be superimposed on the high-magnification image Dh in combination. That is, in the first embodiment, at least one of a scanning position of a tomographic image, a position irradiated with a laser beam, a fundus shape distribution, and a retina sensitivity distribution is superimposed on the high-magnification image Dh.

Note that a single wide-angle SLO image is used as the low-magnification image Dl in the first embodiment; however, the present invention is not limited to this configuration. For example, a combined image obtained by performing alignment of the low-magnification images Dli captured at different positions may be used as the low-magnification image Dl and then the high-magnification image Dh is aligned to this low-magnification image Dl. In this case, because scanning position information of an eye tomographic image is superimposed on the low-magnification image Dl, the scanning position information of the eye tomographic image can be superimposed on the high-magnification image Dh.

With the configuration described above, the ophthalmological apparatus 10 acquires an adaptive optics SLO image and an SLO image of an eye on which a scanning position of an eye tomographic image is superimposed. The ophthalmological apparatus 10 determines whether the intermediate-magnification image Dm needs to be acquired and determines a capture magnification and a capture position at which the intermediate-magnification image Dm is to be captured, on the basis of a difference in capture magnification between the high-magnification image Dh and the low-magnification image Dl and a capture position of the high-magnification image Dh. The ophthalmological apparatus 10 acquires the intermediate-magnification image Dm if needed. The ophthalmological apparatus 10 then performs alignment of images having close magnifications sequentially from the image having the lowest magnification, on the basis of an image feature that is common to the images. In this way, the ophthalmological apparatus 10 decides a relative position of the high-magnification image Dh on the low-magnification image Dl.

Through this process, images of an eye that have greatly different angles of view or pixel sizes may be accurately aligned.

Second Embodiment

In a second embodiment, the following case will be described. An adaptive optics SLO image is acquired as the high-magnification image Dh and a wide-angle tomographic image is acquired as the low-magnification image Dl. Whether the intermediate-magnification image Dm needs to be acquired and a capture magnification and a capture position at which the intermediate-magnification image Dm is to be captured are determined on the basis of a result obtained by extracting features from the high-magnification image Dh and the low-magnification image Dl. The intermediate-magnification image Dm is acquired if needed. Then, alignment of images of close magnifications is performed sequentially from an image with the lowest magnification, on the basis of an image feature that is common to the images. In this way, a relative position of the high-magnification image Dh on the low-magnification image Dl is decided.

Through this process, tomographic images of an eye that have greatly different angles of view or pixel sizes may be accurately aligned.

In the second embodiment, a case where a scanning position of a wide-angle tomographic image is superimposed on the high-magnification image Dh and the displayed slice of the wide-angle tomographic image is changed in response to movement of the scanning position made by an operator will be described as an example of displaying aligned images of the eye that have greatly different angles of view and pixel sizes.

Figure 2B:
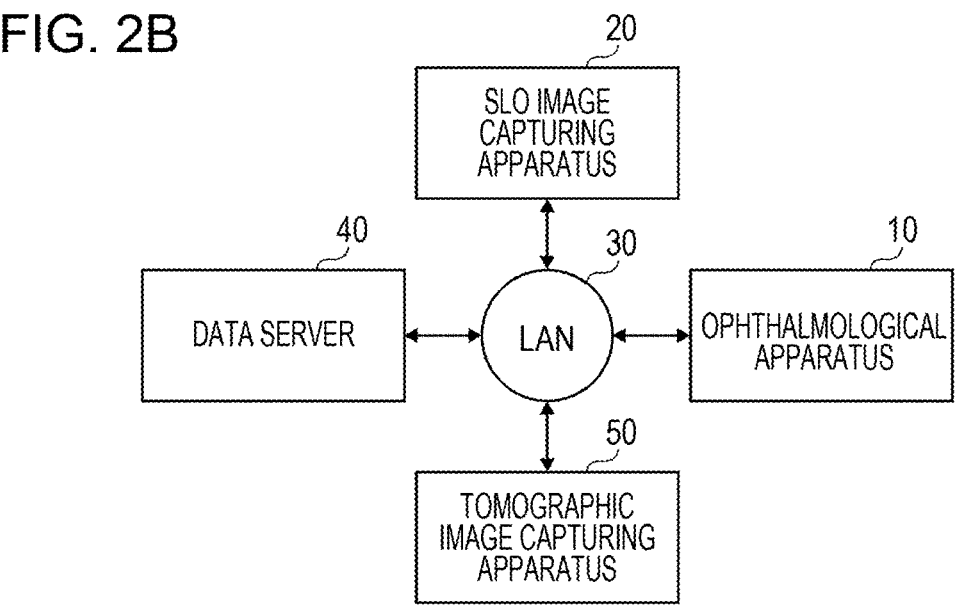

FIG. 2B illustrates the configuration regarding apparatuses connected to the ophthalmological apparatus 10 according to the second embodiment. In the second embodiment, the ophthalmological apparatus 10 is connected to a tomographic image capturing apparatus 50 as well as the SLO image capturing apparatus 20 and the data server 40, which is different from the first embodiment. The tomographic image capturing apparatus 50 is an apparatus that captures tomographic images of the eye and is, for example, a time-domain or Fourier-domain optical coherence tomography (OCT). The tomographic image capturing apparatus 50 three-dimensionally captures tomographic images of a subject's eye (not illustrated) in response to an operation performed by an operator (not illustrated). The captured tomographic images are transmitted to the ophthalmological apparatus 10.

The data server 40 holds therein the low-magnification image Dl, intermediate-magnification image Dm, and high-magnification image Dh of a subject's eye; capturing condition data such as the fixation positions Fl, Fm, and Fh used during capturing of these images; image features of the eye; and normal values related to a distribution of image features of the eye. In the second embodiment, the optic disc, the retinal blood vessels, the photoreceptor cells P, the capillaries Q, and the blood cells W are handled as image features; however, the image features are not limited to these, and for example, image features related to the axon of the ganglion cells or the laminar pores may be handled. Image features of the eye output by the ophthalmological apparatus 10 are stored in the data server 40. Also, in response to a request received from the ophthalmological apparatus 10, the data server 40 transmits the image features of the eye and normal value data related to a distribution of image features to the ophthalmological apparatus 10.

Figure 11:
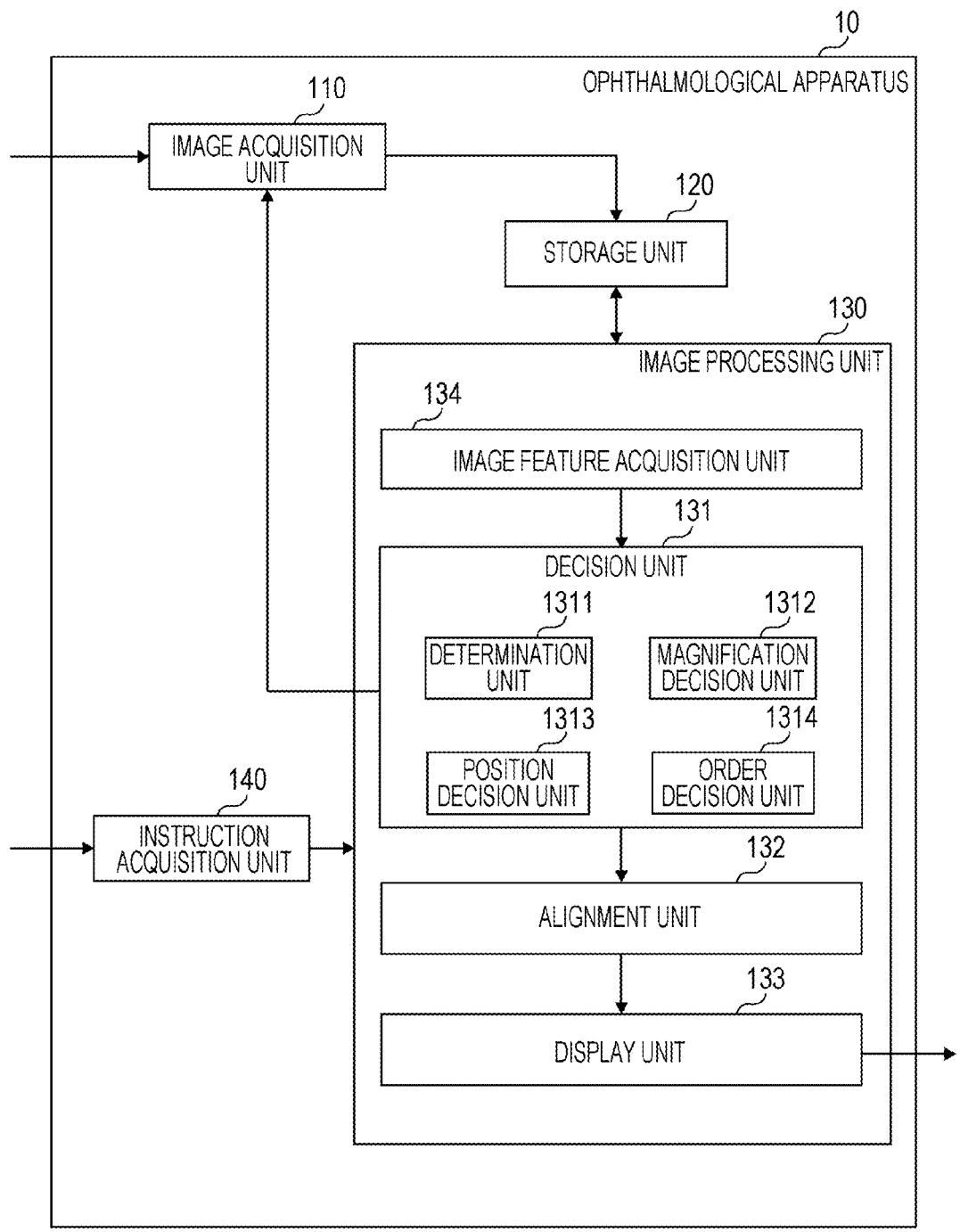
FIG. 11 is a block diagram illustrating an example of the functional configuration of an ophthalmological apparatus according to a second embodiment of the present invention.

FIG. 11 illustrates functional blocks of the ophthalmological apparatus 10 according to the second embodiment. An image feature acquisition unit 134 is included in the image processing unit 130, which is different from the first embodiment.

Figure 12:
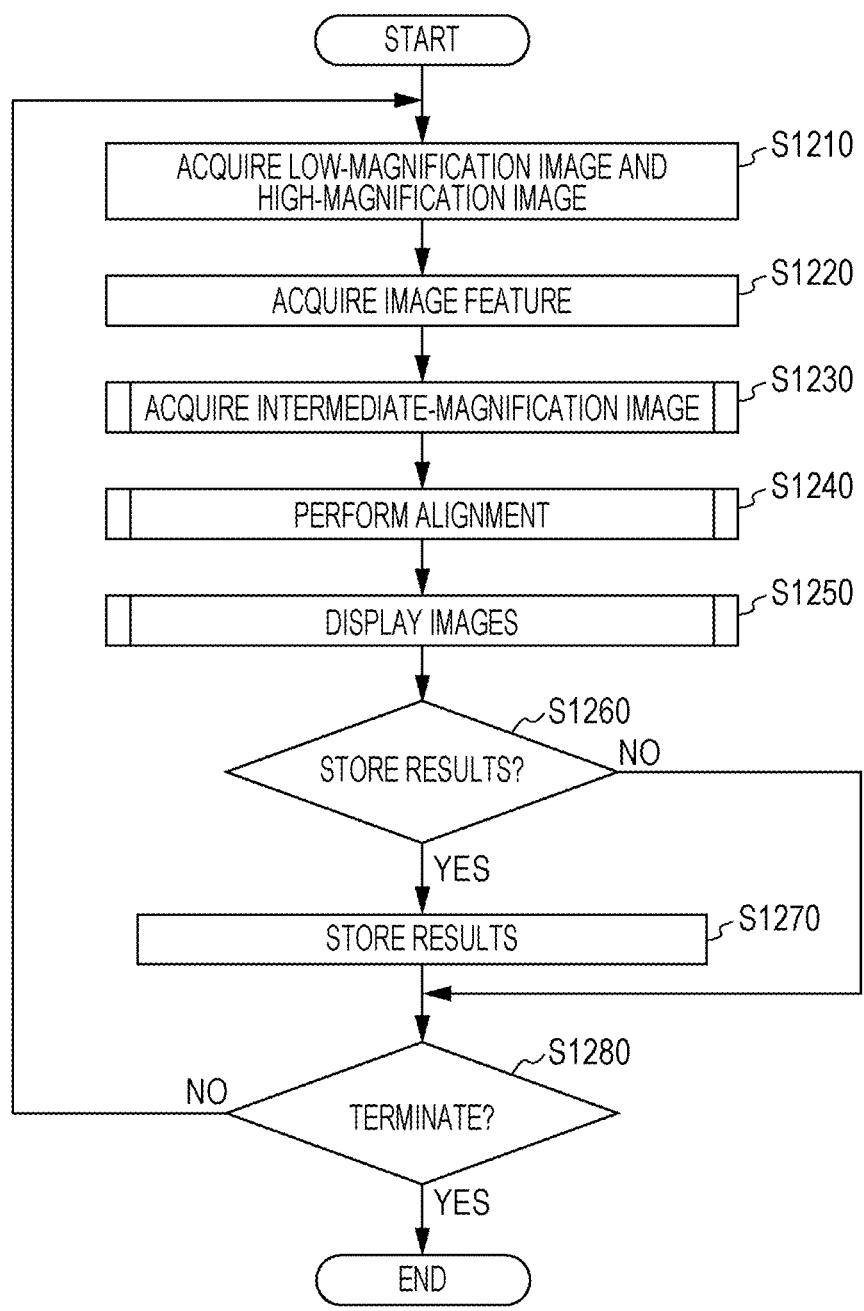
FIG. 12 is a flowchart illustrating an example of a process performed by the ophthalmological apparatus according to the second embodiment of the present invention.

A flow of image processing performed in the second embodiment is as illustrated in FIG. 12. Steps are similar to those of the first embodiment except for steps S1220, S1230, S1240, and S1250. Therefore, in the second embodiment, only steps S1220, S1230, S1240, and S1250 will be described.

Step S1220

The image feature acquisition unit 134 detects the optic disc and the vascular arcade from the low-magnification image Dl and the photoreceptor cells P and the capillaries from the high-magnification image Dh. That is, the image feature acquisition unit 134 acquires image features from images of different magnifications.

First, a process of detecting the optic disc is performed in the following procedure.

i) Optic disc template images obtained by capturing the optic disc of healthy subjects with the SLO apparatus are prepared in advance. A rough position of the optic disc is detected through template matching based on the template images.

ii) A deformable model is applied to the position obtained in step i). A position of the deformation-completed deformable model is set as a boundary of the optic disc area.

Note that the method used in the optic disc detection process is not limited to the above-described one, and any given available method may be used.

Next, a process of detecting a vascular arcade is performed in the following procedure. The retinal blood vessel has a line-like structure. Thus, a filter that enhances the line-like structure is used to extract the retinal blood vessels. Specifically, smoothing is performed on the low-magnification image Dl by using a Gaussian function of a size σ equivalent to the radius of the vascular arcade. A line enhancement filter based on the Hessian matrix is then applied to the low-magnification image Dl. The low-magnification image D is then binarized based on a threshold Ta. In this way, the vascular arcade is extracted. Note that the method used to detect blood vessels is not limited to this one, and any given available method may be used.

A process of detecting photoreceptor cells is performed in a procedure including 1) high-frequency noise reduction process and 2) image binarization.

In step 1), for example, frequency conversion is performed on the high-magnification image Dh using fast Fourier transform (FFT). Then, a low-pass filter is applied to the high-magnification image Dh so as to reduce high-frequency component signal values. Inverse Fourier transform is then performed on the resulting high-magnification image Dh so as to return the domain of the high-magnification image Dh to the spatial domain. In this way, the high-magnification image Dh with reduced high-frequency components is generated.

In step 2), the noise-reduced high-magnification image Dh generated in step 1) is binarized based on a threshold Tb so as to detect the photoreceptor cells P.

Capillaries are identified as regions where blood cell components move in the following procedure from the high-magnification image Dh.

a) Differentiating processing is performed on adjacent frames of the high-magnification image Dh whose frames have been aligned (a differential moving image is generated).

b) A luminance statistical value (variance) between the frames is calculated at each x-y position of the differential moving image generated in step a).

c) A region where the luminance variances at the respective x-y positions of the differential moving image are greater than or equal to a threshold Tv is identified as a region where blood cells have moved, that is, a capillary region.

Note that a method used in the capillary vessel detection process is not limited to this method, and any given available method may be used. For example, a filter that enhances the line-like structure may be applied to a specific frame of the high-magnification image Dh so as to detect a blood vessel.

Step S1230

The decision unit 131 determines whether the intermediate-magnification image Dm needs to be acquired, which has an intermediate resolution between a resolution of the low-magnification image Dl and a resolution of the high-magnification image Dh. If the decision unit 131 determines that the intermediate-magnification image Dm needs to be acquired, the decision unit 131 decides a capture magnification at which, a capture position at which, and a capture order in which the intermediate-magnification image Dm is to be captured. Also, the decision unit 131 requests the image acquisition unit 110 to acquire the intermediate-magnification image Dm. In response to this request, the image acquisition unit 110 acquires the intermediate-magnification image Dm.

Figure 13:
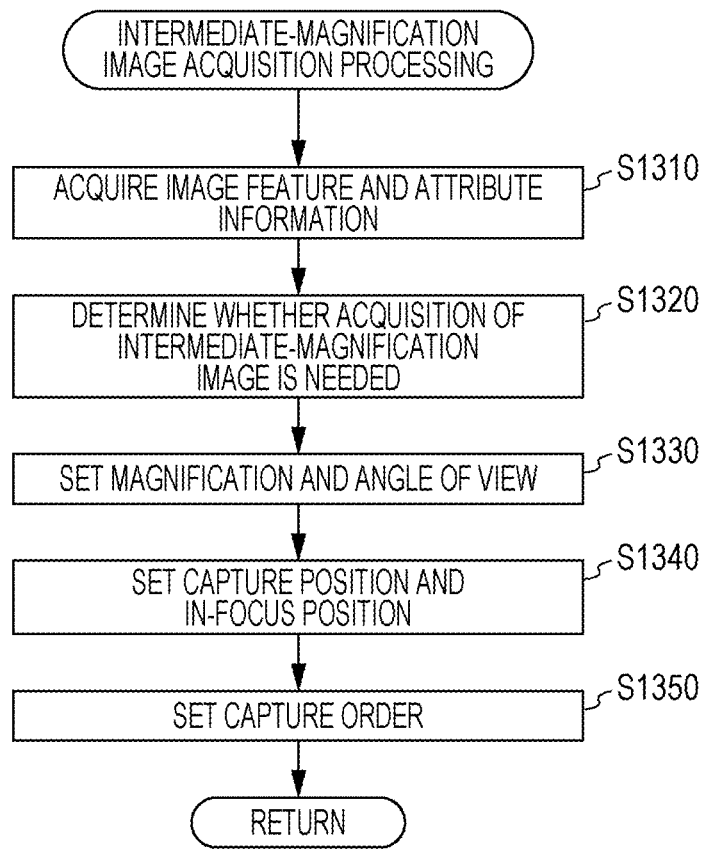
FIG. 13 is a flowchart illustrating an example of details of processing performed in step S1230 in the second embodiment of the present invention.

Processing performed in step S1230 will be described in detail later with reference to a flowchart illustrated in FIG. 13.

Step S1240

The alignment unit 132 performs alignment of the low-magnification image Dl and the high-magnification image Dh. In the case where the intermediate-magnification image Dm has been acquired in step S1230, the position of the high-magnification image Dh on the low-magnification image Dl is decided using the intermediate-magnification image Dm. Here, the alignment unit 132 corresponding to an example of an alignment unit decides an order in which alignment is performed on images, on the basis of at least one of, the images, the capture conditions of the images, and image features of the images.

Processing of step S1240 is performed in a manner similar to that of the first embodiment. However, in the case where feature extraction has been performed on the low-magnification image Dl and the high-magnification image Dm in step S1220 and also on the intermediate-magnification image Dm, the resulting feature values may be used as an alignment evaluation function. Feature-based alignment can implement faster alignment than pixel-value-based alignment.

Step S1250

The display unit 133 superimposes the high-magnification image Dh on the low-magnification image Dl on the basis of the alignment parameter value obtained in step S1240 as illustrated in FIG. 6H. In the second embodiment, the low-magnification image Dl is a three-dimensional tomographic image. Thus, a projection image (mean value projection image) is generated along the z-axis direction of the low-magnification image Dl, and the high-magnification image Dh is superimposed on the projection image. In the second embodiment, a specific scanning position on the low-magnification image Dl is displayed as a cross-shaped arrow on the projection image. A tomographic image resulting from sectioning at the position of the arrow is displayed along with the superimposed image (of the high-magnification image Dh and the projection image).

Because scanning position information of an eye tomographic image is superimposed on the projection image, the scanning position information of the eye tomographic image is superimposed on the high-magnification image Dh. Further, because the operator is allowed to (vertically or horizontally) move the arrow, which represents the position of the displayed tomographic image, via the instruction acquisition unit 140, the sectioned (displayed) tomographic image changes in response to the operation.

Note that the method used to generate the projection image is not limited to the mean value projection, and any given projection method may be used. For example, maximum intensity projection (MIP) may be used. Alternatively, the image feature acquisition unit 134 may obtain a layer boundary. A projection image of a specific tissue or lesion may be generated by limitedly performing projection at a specific boundary between layers.

Also, the high-magnification image Dh is not limited to a still image and may be a moving image.

Further, in the second embodiment, the scanning position of the eye tomographic image is used as information superimposed on the high-magnification image Dh; however, the information superimposed is not limited to this one. For example, as illustrated in FIG. 6F, a map of retina sensitivity values may be superimposed on the high-magnification image Dh. Alternatively, as illustrated in FIG. 6E, a map of fundus shape measurement values may be superimposed on the high-magnification image Dh. Alternatively, as illustrated in FIG. 6G, a map of a position irradiated with a therapeutic laser beam may be superimposed on the high-magnification image Dh. In this case, the high-magnification image Dh may be displayed as a moving image, which enables observation of a relationship between the position irradiated with the laser beam and movement of blood cells or a change in shape of blood vessels. Further, a plurality of pieces of information among the above-described maps may be superimposed on the high-magnification image Dh in combination.

Referring next to the flowchart illustrated in FIG. 13, the processing performed in step S1230 will be described in detail.

Step S1310

The decision unit 131 acquires the image features of the eye that have been acquired by the image feature acquisition unit 134 and attribute information from the storage unit 120.

Specifically, the decision unit 131 acquires the optic disc and the vascular arcade region as the image features of the low-magnification image Dl and the photoreceptor cells P and the capillary region as the image features of the high-magnification image Dh.

The decision unit 131 acquires, as attribute information of the low-magnification image Dl and the high-magnification image Dh, the angle of view [μm], the pixel size [μm/pixel], the fixation position, the in-focus position, the frame rate [frames/sec], the number of frames [frames], and the acquisition date and time. Note that specific attribution information is the same as that of the first embodiment, and thus a description thereof is omitted.

Step S1320

The determination unit 1311 determines whether the intermediate-magnification image Dm needs to be acquired. In the second embodiment, the determination unit 1311 determines that the intermediate-magnification image Dm needs to be acquired if there is no common image feature that is common to the image features of the low-magnification image Dl and the high-magnification image Dh that have been acquired in step S1310. If there is a common image feature, the determination unit 1311 determines that the intermediate-magnification image Dm need not be acquired.

In the second embodiment, there is no common image feature, and thus the determination unit 1311 determines that the intermediate-magnification image Dm needs to be acquired.

In order to speed up the processing of step S1320, a list of image features frequently observed at each of magnifications of captured images may be used to determine whether the intermediate-magnification image Dm needs to be acquired as in the first embodiment.

Step S1330

If it is determined in step S1320 that the intermediate-magnification image Dm needs to be acquired, the magnification decision unit 1312 sets a magnification (angle of view and pixel size) of the intermediate-magnification image Dm.

The magnification of the intermediate-magnification image Dm is set basically in the same manner as that of step S730 of the first embodiment except for the following two points.

In processing i) of step S730, feature extraction is performed on an image having the highest magnification, among the intermediate-magnification images Dm including a common image feature in common with the low-magnification image Dl in the image feature list. If the image feature written in the list is extracted, the highest magnification is set as a first intermediate magnification. If the image feature is not extracted, an intermediate-magnification image having a lower magnification is selected and the similar determination process is performed (until the image feature is extracted). In this way, the first intermediate magnification is set. If the image feature is not extracted even when all the selectable intermediate-magnification images Dm (including a common image feature in common with the low-magnification image Dl in the list) are used, a magnification of the intermediate-magnification image Dm that is closest to the magnification of the low-magnification image Dl is set as the first intermediate magnification.

Feature extraction is similarly performed on an image having the lowest magnification, among the intermediate-magnification images Dm including a common image feature in common with the high-magnification image Dh. If the image feature written in the image feature list is extracted, the lowest magnification is set as a second intermediate magnification. If the image feature is not extracted, an intermediate-magnification image having a higher magnification is selected and the similar determination process is performed (until the image feature is extracted). In this way, the second intermediate magnification is set. If the image feature is not extracted even when all the selectable intermediate-magnification images Dm (including a common image feature in common with the high-magnification image Dh in the image feature list) are used, a magnification of the intermediate-magnification image Dm that is closest to the magnification of the high-magnification image Dh is set as the second intermediate magnification.

Then, in processing ii) of step S730, instead of checking whether an image feature that is common to both the intermediate-magnification images is on the image feature list, feature extraction is performed on both the intermediate-magnification images. If there is a common image feature, the magnifications of the intermediate-magnification images are set as intermediate magnifications.

In the second embodiment, the angle of view and the pixel size associated with the magnification number 2 are respectively selected as the angle of view and the pixel size of a first-intermediate-magnification image including a common image feature (vascular arcade) in common with the low-magnification image Dl (with the magnification number 1 in the image feature list). Specifically, as the angle of view and the pixel size of the first-intermediate-magnification image, an angle of view of 1600×1600 [μm] and a pixel size of 4.0×4.0 [μm/pixel] are respectively selected. Then, as in step S1220, a line structure enhancement filter is used to extract a vascular arcade or thin arteries and veins. Also, the angle of view and the pixel size associated with the magnification number 3 are respectively selected as the angle of view and the pixel size of a second-intermediate-magnification image including a common image feature (capillaries) in common with the high-magnification image Dh (with the magnification number 4). Specifically, as the angle of view and the pixel size of the second-intermediate-magnification image, an angle of view of 800×800 [μm] and a pixel size of 2.0×2.0 [μm/pixel] are respectively selected. Then, as in step S1220, the line structure enhancement filter is used to extract capillaries or thin arteries and veins. There is a common image feature for the magnification numbers 2 and 3, and thus these magnifications are set as the intermediate magnifications. Then, the process proceeds to step S1340.

As described above, the decision unit 131 corresponding to an example of a decision unit decides a method for capturing the intermediate-magnification images on the basis of the image feature.

Note that the feature extraction processing is not a requirement of this step, the magnification (angle of view and pixel size) of the intermediate-magnification image Dm may be set using the same method as that used in the first embodiment in order to perform processing of step S1330 at a higher speed.

Step S1340

The position decision unit 1313 sets capture positions and in-focus positions of the intermediate-magnification images Dmj having the magnifications (angles of view and pixel sizes) set in step S1330.

In order to decide the capture positions of the intermediate-magnification images Dmj, data of the fixation position, angle of view, and pixel size of the high-magnification image Dh and the image features of the low-magnification image Dl that have been acquired in step S1310 are used in the second embodiment.

Among settings regarding capture positions of the intermediate-magnification images Dmj, a method for setting capture positions of the intermediate-magnification image D2j associated with the magnification number 2 will be described. Specifically, it is determined whether the low-magnification image Dl includes an image feature at the capture position of the high-magnification image Dh. If there is no image feature, the intermediate-magnification images D2j are captured by sequentially moving the capture position in a direction for which the number of the intermediate-magnification images D2j to be captured in a range from the capture position of the high-magnification image Dh to a region including the image feature is smallest. At this time, the capture position is sequentially moved by a certain distance so that the adjacent intermediate-magnification images D2j overlap by a certain amount.

In the second embodiment, because there is no vascular arcade at the capture position (parafovea) of the high-magnification image Dh, the intermediate-magnification images D2j associated with the magnification number 2 are captured by sequentially moving the fixation position in the vertical direction so that the intermediate-magnification images D2j include the vascular region. At this time, the fixation position is sequentially moved by a certain distance so that the adjacent intermediate-magnification images D2j overlap by a quarter of their widths. A plurality of dotted-line rectangular areas arranged in the vertical direction in FIG. 8A represent the intermediate-magnification images D2j.

The capture position of the intermediate-magnification image D3 associated with the magnification number 3 is set to be the same as the capture position of the high-magnification image Dh as in the first embodiment.

Also, the in-focus position is set to be the same as the in-focus position of the high-magnification image Dh. Note that a method used to set the in-focus position is not limited to this one, and any given method may be used.

Step S1350

The order decision unit 1314 decides an order in which the intermediate-magnification images Dmj decided in steps S1320 to S1340 are to be captured.

In the second embodiment, it is assumed that intermediate-magnification images are captured in ascending order of magnification. In the case where a plurality of intermediate-magnification images of the same magnification are captured, capturing is started from a position including a large image feature and is sequentially performed from the closest fixation position. The capture order of the intermediate-magnification images is not limited to this one and may be set using any given setting method.

In the second embodiment, the intermediate-magnification image capturing method is decided on the basis of the policy "a) by fixing the capture magnification or selecting the capture magnification from options and by making the capture position settable to a given position" (FIG. 8A) as in the first embodiment; however, the policy used in the decision is not limited to this one. For example, the decision may be made based on the policy "b) by making the capture magnification settable to a given value and by setting the capture position to be the same as that of the high-magnification image Dh" described in the first embodiment. When the method b) is used, whether the intermediate-magnification image Dm needs to be acquired and the capture magnification and in-focus position of the intermediate-magnification image Dm are automatically selected on the basis of settings regarding the capture magnification (angle of view and pixel size), capture position, and in-focus position of the high-magnification image Dh selected by an operator.

With the configuration described above, the ophthalmological apparatus 10 acquires an adaptive optics SLO image and a wide-angle tomographic image. The ophthalmological apparatus 10 determines whether the intermediate-magnification image Dm needs to be acquired, the capture magnification and capture position at which the intermediate-magnification image is to be captured, on the basis of a result obtained by extracting features from the high-magnification image Dh and the low-magnification image Dl.

Through this process, images of an eye that have greatly different angles of view or pixel sizes may be accurately aligned.

Third Embodiment

In a third embodiment, the following case will be described. An adaptive optics tomographic image is acquired as the high-magnification image Dh and a wide-angle tomographic image is acquired as the low-magnification image Dl. Whether the intermediate-magnification image Dm needs to be acquired and a capture magnification and a capture position at which the intermediate-magnification image Dm is to be captured are determined on the basis of a result obtained by extracting features from the high-magnification image Dh and the low-magnification image Dl. The intermediate-magnification image Dm is acquired if needed. Then, alignment of images of close magnifications is performed sequentially from an image with the lowest magnification, on the basis of an image feature that is common to the images. In this way, a relative position of the high-magnification image Dh on the low-magnification image Dl is decided.

Through this process, tomographic images of an eye that have greatly different angles of view or pixel sizes may be accurately aligned.

In the third embodiment, a case where a scanning position of a wide-angle tomographic image is superimposed on the high-magnification image Dh will be described as an example of displaying aligned images of the eye that have greatly different angles of view and pixel sizes.

Figure 2C:
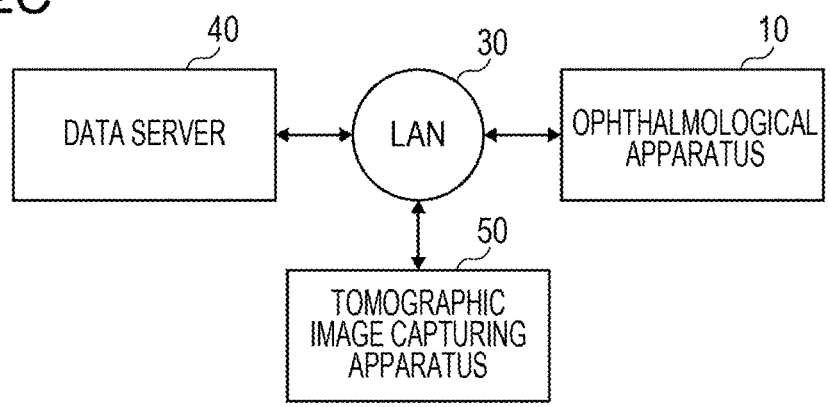

FIG. 2C illustrates the configuration regarding apparatuses connected to the ophthalmological apparatus 10 according to the third embodiment. In the third embodiment, the ophthalmological apparatus 10 is connected to the tomographic image capturing apparatus 50 including an adaptive optics system, which is different from the first embodiment. The functional block diagram of the ophthalmological apparatus 10 according to the third embodiment is the same as that of the second embodiment, and thus a description thereof will be omitted.

It is assumed that the data server 40 holds therein image features of the eye and normal value data related to a distribution of the image features of the eye, as in the second embodiment.

Figure 14:
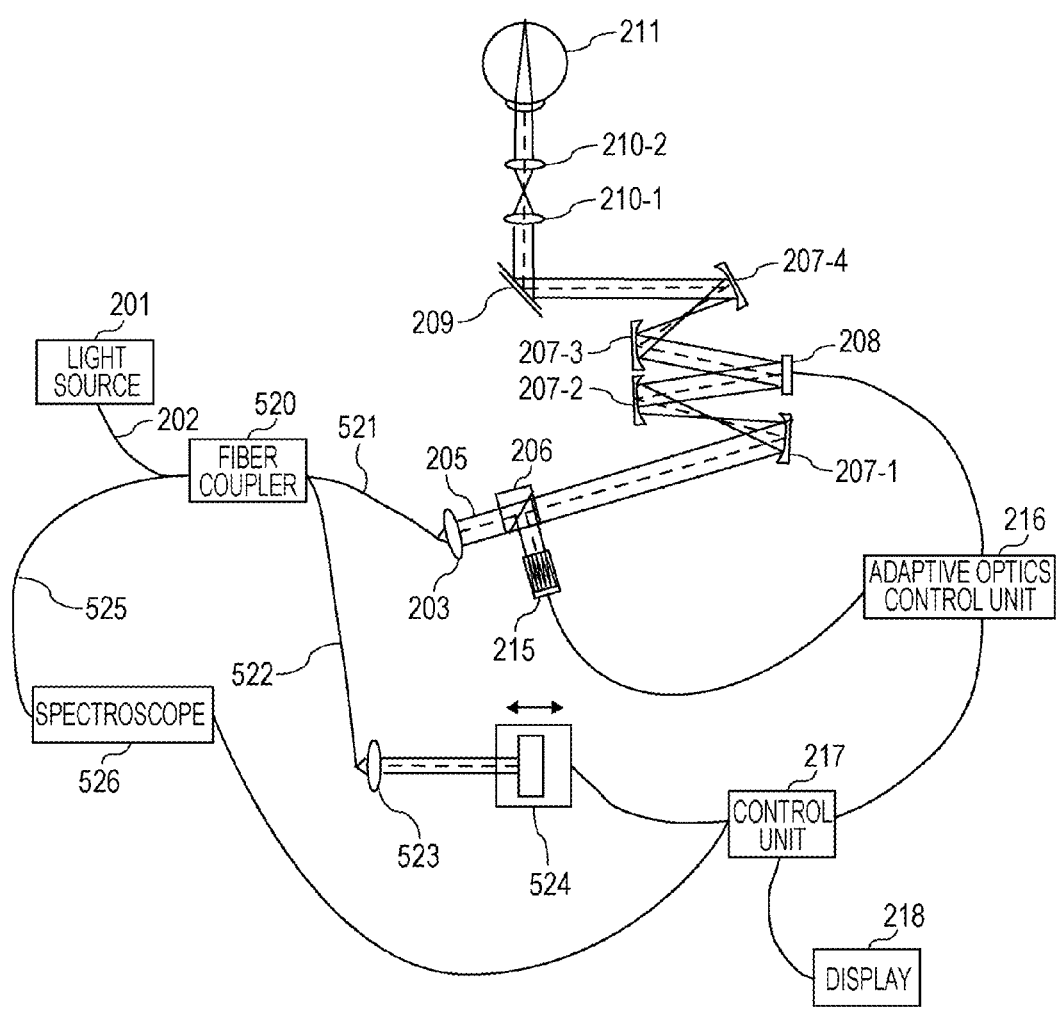
FIG. 14 is a diagram illustrating an example of the configuration of a tomographic image capturing apparatus according to a third embodiment of the present invention.

Referring next to FIG. 14, the configuration of the tomographic image capturing apparatus 50 including an adaptive optics system will be described. Referring to FIG. 14, the tomographic image capturing apparatus 50 includes a light source 201. In the third embodiment, an SLD light source of a wavelength of 840 nm is used. The light source 201 may be of a low-coherence type, and an SLD light source of a wavelength of 30 nm or longer may be preferably used. Alternatively, an ultrashort pulse laser, such as a titanium-sapphire laser, may be used as the light source 201. Light radiated from the light source 201 propagates through a single-mode optical fiber 202 to be led to a fiber coupler 520. The light is branched by the fiber coupler 520 to a measurement light path 521 and a reference light path 522. A fiber coupler having a branching fraction of 10:90 is used to make 10% of the incident light go to the measurement light path 521. The light that has passed through the measurement light path 521 is radiated as measurement light 205 of parallel rays by a collimator 203. The configuration downstream the collimator 203 is the same as that of the first embodiment. Specifically, the light is radiated to an eye 211 through an adaptive optics system and a scanning optical system 209, and the light reflected or scattered by the eye 211 propagates through the same path again, is led by the optical fiber 521, and reaches the fiber coupler 520. On the other hand, reference light that has passed through the reference light path 522 is emitted by a collimator 523, is reflected by an optical-path length changing unit 524, and returns to the fiber coupler 520. The measurement light and the reference light that have reached the fiber coupler 520 are combined, and the resulting light is led to a spectroscope 526 through an optical fiber 525. Based on information of coherent light obtained by separation by the spectroscope 526, a control unit 217 constructs a tomographic image of the eye 211. The control unit 217 is capable of capturing an image of a desired depth by controlling the optical-path length changing unit 524.

By increasing the swinging angle of the scanning optical system 209 and instructing an adaptive optics control unit 216 not to perform aberration correction in the configuration illustrated in FIG. 14, the tomographic image capturing apparatus 50 can operate as an ordinary tomographic image capturing apparatus and capture a wide-angle tomographic image (low-magnification image Dl).

Also, in the third embodiment, the tomographic image capturing apparatus 50 including an adaptive optics system is configured as a spectral domain optical coherence tomography (SD-OCT); however, the tomographic image capturing apparatus 50 is not required to be SD-OCT and may be configured as a swept source optical coherence tomography (SS-OCT). In the case of SS-OCT, a light source that generates light of different wavelengths at different times is used and the spectroscope 526 for obtaining spectrum information is no longer needed. Also, SS-OCT can capture high-penetration images including not only the retina but also the choroid.

A flow of image processing performed by the ophthalmological apparatus 10 according to the third embodiment is similar to that of the second embodiment except for steps S1220, S1230, S1240, and S1250. Thus, in the third embodiment, only processing of steps S1220, S1230, S1240, and S1250 will be described.

Step S1220

The image feature acquisition unit 134 extracts, as image features, the inner limiting membrane, the optic nerve fiber layer boundary, the ganglion cell layer boundary, the inner plexiform layer boundary, the outer plexiform layer boundary, the photoreceptor cell inner segment-outer segment boundary, the retinal pigment epithelium boundary, the optic disc, the fovea, and the retinal vessels from the low-magnification image Dl, that is, a three-dimensional eye tomographic image, stored in the storage unit 120. Note that the retinal vessel region is identified as a region projected on the x-y plane. The image feature acquisition unit 134 then acquires the inner limiting membrane B1, the inner plexiform layer boundary B4, the photoreceptor cell inner segment-outer segment boundary B5, the retinal pigment epithelium boundary B6, and the fovea F1 from among the extracted image features, as illustrated in FIG. 6A. The image feature acquisition unit 134 also stores the acquired image features in the storage unit 120.

Now, a procedure of extracting a feature from the low-magnification image Dl will be specifically described.

First, a procedure of extracting a boundary between layers will be described. Note that it is assumed herein that a three-dimensional tomographic image to be processed is a set of two-dimensional tomographic images (B-scan images). The following processing is performed on each of the two-dimensional tomographic images. First, smoothing processing is performed on a two-dimensional tomographic image of interest so as to reduce noise components. Then, edge components are detected in the two-dimensional tomographic image. Some line segments are extracted as layer boundary candidates, on the basis of their connectivity. Among the extracted candidates, the topmost line segment is extracted as the inner limiting membrane B1, the second topmost line segment is extracted as the optic nerve fiber layer boundary B2, and the third topmost line segment is extracted as the inner plexiform layer boundary B4. Also, a line segment having the highest contrast located on the outer side of the inner limiting membrane B1 (on a side of the larger z coordinate in FIG. 6A) is extracted as the photoreceptor cell inner segment-outer segment boundary B5. Further, the bottommost line segment among the layer boundary candidates is extracted as the retinal pigment epithelium boundary B6. A deformable model, such as Snakes or a level set method, may be applied by using these line segments as initial values so as to perform more precise extraction. Alternatively, the layer boundary may be extracted using a graph cut method. Note that the deformable-model-based or graph-cut-based boundary extraction may be three-dimensionally performed on a three-dimensional tomographic image or two-dimensionally performed on each two-dimensional tomographic image. Alternatively, any given method that enables a boundary between layers to be extracted from an eye tomographic image may be used.

After extracting boundaries between layers from the eye tomographic image, two deepest indentation portions are further detected from the shape of the extracted inner limiting membrane B1. In this way, the optic disc and the fovea are extracted. Here, the shallower indentation portion is extracted as the fovea, and the deeper indentation portion is extracted as the optic disc.

Furthermore, a filter that enhances the line structure is applied to an image obtained by projecting the low-magnification image Dl (eye tomographic image) in the depth direction (z-axis direction) so as to identify a blood vessel region on the x-y plane.

Then, capillaries and photoreceptor cells are extracted as image features from the high-magnification image Dh, that is, a three-dimensional adaptive optics tomographic image.

The capillary region is extracted by applying a filter that enhances the line structure to a mean value projection image with respect to the z-axis direction of the adaptive optics tomographic image. Note that any given available method may be used in the blood vessel extraction processing, and for example, a region with a value less than a threshold T3 may be extracted.

The photoreceptor cells are extracted in a procedure similar to that of step S1220 of the second embodiment from a curved tomographic image which is obtained by sectioning the adaptive optics tomographic image along the photoreceptor cell inner segment-outer segment boundary (IS/OS) or a line located on the slightly outer side (the positive direction of the z-axis) of the photoreceptor cell inner segment-outer segment boundary (IS/OS).

Step S1230

The decision unit 131 determines whether the intermediate-magnification images Dmj need to be acquired, which have intermediate resolutions between a resolution of the low-magnification image Dl and a resolution of the high-magnification image Dh. If the decision unit 131 determines that the intermediate-magnification images Dmj need to be acquired, the decision unit 131 decides capture magnifications at which, capture positions at which, and a capture order in which the intermediate-magnification images Dmj are to be captured. Also, the decision unit 131 requests the image acquisition unit 110 to acquire the intermediate-magnification image Dm. In response to this request, the image acquisition unit 110 acquires the intermediate-magnification image Dm.

As the method for acquiring the intermediate-magnification image Dm, there may be two methods:

1) The image acquisition unit 110 requests the tomographic image capturing apparatus 50 to capture the intermediate-magnification image Dm, and the tomographic image capturing apparatus 50 transfers the captured intermediate-magnification image Dm to the storage unit 120; and 2) The image acquisition unit 110 requests the data server 40 to transfer the intermediate-magnification image Dm stored in the data server 40, and the data server 40 transfers the intermediate-magnification image Dm. In the third embodiment, the case of using the method 1) will be described.

Note that the present invention is not limited to the case of using the method 1) and may be carried out using the method 2).

Processing performed in step S1230 will be described in detail later with reference to the flowchart illustrated in FIG. 13.

Step S1240

The alignment unit 132 performs alignment of the low-magnification image Dl and the high-magnification image Dh. In the case where the intermediate-magnification images Dmj are acquired in step S1230, the position of the high-magnification image Dh on the low-magnification image Dl is decided using the intermediate-magnification images Dmj.

Processing of step S1240 is basically the same as that of the second embodiment except for the following differences. Both the low-magnification image Dl and the high-magnification image Dh are three-dimensional images, and thus the representative image generation step is not needed; and a three-dimensional correlation coefficient is used as the similarity evaluation function and three-dimensional Affine transformation is used as the coordinate conversion method. Note that the similarity evaluation function and the coordinate conversion method are not limited to these ones, and any given available methods may be used.

Also, in the case where feature extraction has been performed on the low-magnification image Dl and the high-magnification image Dh in step S1220 and also on the intermediate-magnification image Dm, the resulting feature values may be used as an alignment evaluation function. Feature-based alignment can implement faster alignment than pixel-value-based alignment.

Step S1250

The display unit 133 superimposes the high-magnification image Dh on the low-magnification image Dl on the basis of the alignment parameter value obtained in step S1240 as illustrated in FIG. 6H. In the third embodiment, both the low-magnification image Dl and the high-magnification image Dh are three-dimensional tomographic images. Thus, projection images (mean value projection images) of the low-magnification image Dl and the high-magnification image Dh are generated with respect to the z-axis direction. Then, the projection image of the high-magnification image Dh is superimposed on the projection image of the low-magnification image Dl.

Figure 8G:
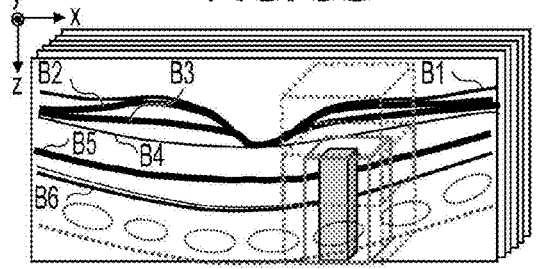
Figure 8H:
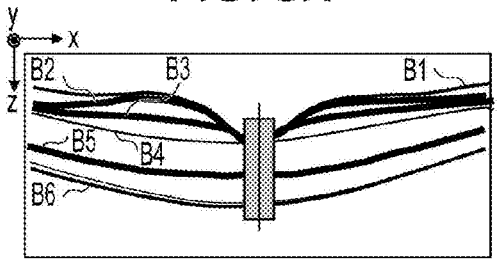

In the third embodiment, a specific scanning position on the low-magnification image Dl is displayed as a cross-shaped arrow on the projection image thereof. A tomographic image resulting from sectioning at the position indicated by the arrow is displayed along with the superimposed image as illustrated in FIG. 6H. FIG. 8H illustrates an example of a wide-angle tomographic image resulting from sectioning at the position indicated by the arrow in the horizontal (x-axis) direction. Referring to FIG. 8H, not only the tomographic image of the low-magnification image Dl but also the high-magnification image Dh and the position of the scanning line in the y-axis direction are superimposed. Note that FIG. 8H illustrates a region near the fovea included in the wide-angle tomographic image for ease of explanation.

In the third embodiment, scanning position information of an eye tomographic image is superimposed on the high-magnification image Dh as illustrated in FIG. 6H. Further, because the operator is allowed to (vertically or horizontally) move the arrow, which represents the position of the displayed tomographic image illustrated in FIG. 6H, via the instruction acquisition unit 140, the sectioned (displayed) slices of the low-magnification image Dl and the high-magnification image Dh change in response to the operation.

In the case where a plurality of high-magnification images Dh are captured at different fixation positions as illustrated in FIG. 8D, a method similar to that used in the first embodiment is used to perform adjustment so as to make the high-magnification images Dhk have similar luminance characteristics. Specifically, luminances of the high-magnification images Dhk are adjusted so that the high-magnification images Dhk have similar luminance characteristics, and the resulting high-magnification images Dhk are displayed on the low-magnification image Dl. Further, in the case where the high-magnification images Dhk are captured at close positions and thus have overlaps (including the case where the capture positions are the same), one of the following methods is used to display the overlapping regions. Specifically, the image quality index of each image is calculated and the image with the highest evaluation value is displayed. Alternatively, the high-magnification images Dhk are displayed as semi-transparent images and luminances thereof are blended. Any given available image quality index value may be used. In the third embodiment, the average luminance of the image histogram is used.

Note that the method used to generate the projection image is not limited to the mean value projection, and any given projection method may be used. For example, maximum intensity projection (MIP) may be used. Alternatively, the image feature acquisition unit 134 may obtain a layer boundary. A projection image of a specific tissue or lesion may be generated by limitedly performing projection at a specific layer boundary.

Also, the high-magnification image Dh is not limited to a still image and may be a moving image.

In the third embodiment, the scanning position of the eye tomographic image is used as information superimposed on the high-magnification image Dh; however, the information superimposed is not limited to this information. For example, as illustrated in FIG. 6F, a map of retina sensitivity values may be superimposed on the high-magnification image Dh. Alternatively, as illustrated in FIG. 6E, a map of fundus shape measurement values may be superimposed on the high-magnification image Dh. Alternatively, as illustrated in FIG. 6G, a map of a position irradiated with a therapeutic laser beam may be superimposed on the high-magnification image Dh. In this case, the position irradiated with the laser beam and a distribution of blood vessels including a blood vessel lesion can be collectively observed. Further, a plurality of pieces of information among the above-described maps may be superimposed on the high-magnification image Dh in combination.

Referring next to the flowchart illustrated in FIG. 13, processing performed in step S1230 will be described in detail. Note that step S1350 is the same as that of the second embodiment, and thus a description thereof will be omitted.

Step S1310

The decision unit 131 acquires the image features of the eye that have been acquired by the image feature acquisition unit 134 in step S1220 and attribute information from the storage unit 120.

Specifically, the decision unit 131 acquires the optic disc and the vascular arcade region as the image features of the low-magnification image Dl and the photoreceptor cells P and the capillary region as the image features of the high-magnification image Dh.

The decision unit 131 acquires, as attribute information of the low-magnification image Dl and the high-magnification image Dh, the angle of view [μm], the pixel size [μm/pixel], the fixation position, the coherence gate position, the frame rate [frames/sec], the number of frames [frames], and the acquisition date and time.

In the third embodiment, the low-magnification image Dl has attribute information, such as an angle of view of 12800×6400×1600 [μm], a pixel size of 20.0×20.0×5.0 [μm/pixel], a fixation position indicating the fovea, a coherence gate position indicating the retinal inner layer, and acquisition date and time indicating Nov. 11, 2011 11:11:11. The high-magnification image Dh has attribute information, such as an angle of view of 400×400×400 [μm], a pixel size of 1.0×1.0×1.0 [μm/pixel], a fixation position indicating the parafovea, a coherence gate position indicating the retinal inner layer, and acquisition date and time indicating Nov. 11, 2011 11:12:12.

Step S1320

The determination unit 1311 determines whether the intermediate-magnification image Dm needs to be acquired. In the third embodiment, the determination unit 1311 determines that the intermediate-magnification image Dm needs to be acquired if there is no common image feature that is common to the image features of the low-magnification image Dl and the high-magnification image Dh that have been acquired in step S1310. If there is a common image feature, the determination unit 1311 determines that the intermediate-magnification image Dm need not be acquired.

In the third embodiment, there is no common image feature, and thus the determination unit 1311 determines that the intermediate-magnification image Dm needs to be acquired.

In order to speed up the processing of step S1320, a list (illustrated below) of image features frequently observed at each of magnifications of captured images may be used to determine whether the intermediate-magnification image Dm needs to be acquired.

| Magnification number | Angle of view [μm] | Pixel size [μm/pixel] | Image feature (Retina) |
|---|---|---|---|
| 4 | 400 × 400 × 400 | 1.0 × 1.0 × 1.0 | Nerve fibers Capillaries Photoreceptor cells |
| 3 | 800 × 800 × 800 | 2.0 × 2.0 × 2.0 | Capillaries Thin arteries/veins |
| 2 | 1600 × 1600 × 1600 | 4.0 × 4.0 × 4.0 | Thin arteries/veins Vascular arcade |
| 1 | 12800 × 6400 × 1600 | 20.0 × 20.0 × 5.0 | Vascular arcade Optic disc |

The image feature list above is used when SD-OCT is used as the tomographic image capturing apparatus 50. When SS-OCT is used, not only the retina but also the choroid are included in the capturing range. Thus, the following image feature list is used when conditions for capturing the intermediate-magnification image Dm are set. In the image feature list below, image features are written for a corresponding capture position in the depth direction. In the case of the magnification number 1, the capturing range includes both the retina and the choroid, and thus the image features are common.

| Magnification number | Angle of view [μm] | Pixel size [μm/pixel] | Image feature (Retina) | Image feature (Choroid) |
|---|---|---|---|---|
| 4 | 400 × 400 × 400 | 1.0 × 1.0 × 1.0 | Nerve fibers Capillaries Photoreceptor cells | Choriocapillaris |
| 3 | 800 × 800 × 800 | 2.0 × 2.0 × 2.0 | Capillaries Thin arteries/veins | Choriocapillaris Choroidal blood vessels |

-continued

| Magnification number | Angle of view [µm] | Pixel size [µm/pixel] | Image feature (Retina) | Image feature (Choroid) |
|---|---|---|---|---|
| 2 | 1600 × 1600 × 1600 | 4.0 × 4.0 × 4.0 | Thin arteries/veins Vascular arcade | Choroidal blood vessels |
| 1 | 12800 × 6400 × 1600 | 20.0 × 20.0 × 5.0 | Vascular arcade Optic disc Choroidal blood vessels | |

Step S1330

If it is determined in step S1320 that the intermediate-magnification image Dm needs to be acquired, the magnification decision unit 1312 sets a magnification (angle of view and pixel size) of the intermediate-magnification image Dm.

The magnification of the intermediate-magnification image Dm is set basically in the same manner as in step S1330 of the second embodiment except for that the angle of view and pixel size in the z-axis direction are additionally set.

In the third embodiment, the angle of view and the pixel size associated with the magnification number 2 are respectively selected as the angle of view and the pixel size of a first-intermediate-magnification image including a common image feature (vascular arcade) in common with the low-magnification image Dl (with the magnification number 1 in the image feature list). Specifically, as the angle of view and the pixel size of the first-intermediate-magnification image, an angle of view of 1600×1600×1600 [µm] and a pixel size of 4.0×4.0×4.0 [µm/pixel] are respectively selected. Then, as in step S1220, a line structure enhancement filter is applied to an image obtained by projection in the z-axis direction so as to extract a vascular arcade or thin arteries and veins. Also, the angle of view and the pixel size associated with the magnification number 3 are respectively selected as the angle of view and the pixel size of a second-intermediate-magnification image including a common image feature (capillaries) in common with the high-magnification image Dh (with the magnification number 4). Specifically, as the angle of view and the pixel size of the second-intermediate-magnification image, an angle of view of 800×800×800 [µm] and a pixel size of 2.0×2.0×2.0 [µm/pixel] are respectively selected. Then, as in step S1220, the line structure enhancement filter is applied to an image obtained by projection in the z-axis direction so as to extract capillaries or thin arteries and veins. There is a common image feature for the magnification numbers 2 and 3, and thus these magnifications are set as the intermediate magnifications. Then, the process proceeds to step S1340.

Note that the feature extraction processing is not a requirement of this step, and the magnification (angle of view and pixel size) of the intermediate-magnification image Dm may be set using the image feature list described in step S1320 (as in the first embodiment) in order to perform the processing of step S1330 at a higher speed.

Step S1340

The position decision unit 1313 sets capture positions and coherence gate positions of the intermediate-magnification images Dmj having the magnifications (angles of view and pixel sizes) set in step S1330. Because the tomographic image capturing apparatus 50 is configured as SD-OCT in the third embodiment, both the intermediate-magnification images Dmj include images of the retina in the z-axis direction and the depth-direction capture positions are set to be the same for both the magnifications (the entire retina).

In order to decide the capture positions of the intermediate-magnification images Dmj, data of the fixation position, angle of view, and pixel size of the high-magnification image Dh and the image features of the low-magnification image Dl that have been acquired in step S1310 are used in the third embodiment.

Among settings regarding capture positions of the intermediate-magnification images Dmj, a method for setting capture positions of the intermediate-magnification images D2j associated with the magnification number 2 will be described. Specifically, it is determined whether the low-magnification image Dl includes an image feature at the capture position of the high-magnification image Dh. If there is no image feature, the intermediate-magnification images D2j are captured by sequentially moving the capture position in a direction for which the number of the intermediate-magnification images D2j to be captured in a range from the capture position of the high-magnification image Dh to a region including the image feature is smallest. At this time, the capture position is sequentially moved by a certain distance so that the adjacent intermediate-magnification images D2j overlap by a certain amount.

In the third embodiment, because there is no vascular arcade at the capture position (parafovea) of the high-magnification image Dh, the intermediate-magnification images D2j associated with the magnification number 2 are captured by sequentially moving the fixation position in the vertical direction so that the intermediate-magnification images D2j include the vascular region. At this time, the fixation position is sequentially moved by a certain distance so that the adjacent intermediate-magnification images D2j overlap by a quarter of their widths. A plurality of dotted-line rectangular areas arranged in the vertical direction in FIG. 8A represent the intermediate-magnification images D2j captured in the third embodiment.

The capture position of the intermediate-magnification image D3 associated with the magnification number 3 is set to be the same as that of the high-magnification image Dh as in the first embodiment.

The coherence gate position is set in the following manner. If the coherence gate positions of the low-magnification image Dl and the high-magnification image Dh are the same, this coherence gate position is set. If not, the coherence gate position of each intermediate-magnification image is set to an intermediate position between the coherence gate position of the low-magnification image Dl and the coherence gate position of the high-magnification image Dh. In the third embodiment, the coherence gate is set to the retinal inner layer for both the low-magnification image Dl and the high-magnification image Dh. Thus the coherence gate of each intermediate-magnification image is set to the retinal inner layer. Note that the coherence gate setting method is not limited to this one. The coherent gate position may be set to be the same as the coherence gate position of the low-magnification image Dl or the high-magnification image Dh.

The description has been given in the third embodiment on the assumption that the eye tomographic image is of SD-OCT and thickness of the retina is normal. In the case of SS-OCT, the eye tomographic image is of the high-penetration type, that is, not only the retina but also the choroid located at a deeper position are also included in the image as illustrated in FIG. 8G. For such an image of the high-penetration type, capture positions of intermediate-magnification images are set by changing the capture position not only on the x-y plane but also in the z-axis direction. Referring to FIG. 8G, because the capture position of the high-magnification image Dh is set to the choroid, the z-axis-direction capture position of the intermediate-magnification image Dm is set to be in the vicinity of the choroid by referring to the image feature list. Alternatively, in the case where the retina is thickened because of the influence of a disease such as macular edema, the intermediate-magnification image Dm is captured by sequentially moving the z-axis direction capture position of the intermediate-magnification image Dm by a certain distance relative to the z-axis direction capture position of the high-magnification image Dh toward the capture position of the high-magnification image Dh.

In the third embodiment, the intermediate-magnification image acquisition method is decided on the basis of the policy "a) by fixing the capture magnification or selecting the capture magnification from options and by making the capture position settable to a given position" (FIG. 8A) as in the first embodiment; however, the policy used in the decision is not limited to this one. For example, the decision may be made based on the policy "b) by making the capture magnification settable to a given value and by setting the capture position to be the same as that of the high-magnification image Dh" (FIG. 8B) described in the first embodiment. When the method b) is used, whether the intermediate-magnification image Dm needs to be acquired and the capture magnification and in-focus position of the intermediate-magnification image Dm are automatically selected on the basis of the capture magnification (angle of view and pixel size), capture position, and in-focus position of the high-magnification image Dh selected by an operator.

With the configuration described above, the ophthalmological apparatus 10 acquires an adaptive optics tomographic image and a wide-angle tomographic image. The ophthalmological apparatus 10 determines whether an intermediate-magnification image Dm needs to be acquired, the capture magnification and capture position at which the intermediate-magnification image Dm is to be captured, on the basis of a result obtained by extracting features from the high-magnification image Dh and the low-magnification image Dl. The ophthalmological apparatus 10 acquires the intermediate-magnification image Dm if needed. Then, alignment is performed on images of close magnifications sequentially from the image with the lowest magnification, on the basis of a common image feature. In this way, a relative position of the high-magnification image Dh on the low-magnification image Dl is decided.

Through this process, images of an eye that have greatly different angles of view or pixel sizes may be accurately aligned.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-287253, filed Dec. 28, 2012, which is hereby incorporated by reference herein in its entirety.

What is claimed is:

1. An ophthalmological apparatus comprising:
   an image acquisition unit configured to acquire images of different magnifications;
   a decision unit configured to decide, based on at least the acquired images or capture conditions of the acquired images, a method for capturing an image of an intermediate magnification that is between the magnifications of the acquired images; and
   an alignment unit configured to align the acquired images of different magnifications by using the image of the intermediate magnification captured with the method decided by the decision unit.

2. The ophthalmological apparatus according to claim 1, wherein the decision unit is configured to decide, based on at least the acquired images or the capture conditions of the acquired images, at least one of whether the image of the intermediate magnification needs to be acquired, a capture magnification, an angle of view, a pixel size, a capture position, an in-focus position, and a capture order of the image of the intermediate magnification.

3. The ophthalmological apparatus according to claim 1, further comprising
   an image feature acquisition unit configured to acquire an image feature from the acquired images of different magnifications, wherein
   the decision unit is configured to decide, based on the acquired image feature, the method for capturing the image of the intermediate magnification.

4. The ophthalmological apparatus according to claim 1, wherein the alignment unit is configured to decide an order in which alignment is performed on the acquired images, based on at least one of, the acquired images, the capture conditions of the acquired images, and image features of the acquired images.

5. The ophthalmological apparatus according to claim 1, further comprising
   a display unit configured to adjust luminances of the images so as to make the images have similar luminance characteristics and to display, from among the acquired images of different magnifications, a higher-magnification image on a lower-magnification image.

6. The ophthalmological apparatus according to claim 5, wherein the display unit is configured to superimpose at least one of a scanning position of a tomographic image, a position irradiated with a laser beam, a fundus shape distribution, and a retina sensitivity distribution on the displayed higher-magnification image.

7. The ophthalmological apparatus according to claim 1, further comprising
a control unit configured to control, in a case where images to be displayed on a lower-magnification image among the images have an overlap, at least one of an order in which the images are superimposed, display or non-display of each of the images, and transparencies of the images.

8. The ophthalmological apparatus according to claim 1, wherein at least one of the images of different magnifications is an image generated based on a tomographic image of an eye or a moving image of an eye.

9. An alignment method comprising:
acquiring ophthalmological images of different magnifications;
deciding, based on at least the acquired ophthalmological images or capture conditions of the acquired ophthalmological images, a method for capturing an ophthalmological image of an intermediate magnification that is between the magnifications of the acquired ophthalmological images; and
performing alignment of the acquired ophthalmological images of different magnifications by using the image of the intermediate magnification captured with the decided method.

10. A non-transitory computer storage medium storing thereon a program for causing upon execution one or more processors of a programmable apparatus to execute an alignment method comprising:
acquiring ophthalmological images of different magnifications;
deciding, based on at least the acquired ophthalmological images or capture conditions of the acquired ophthalmological images, a method for capturing an ophthalmological image of an intermediate magnification that is between the magnifications of the acquired ophthalmological images; and
performing alignment of the acquired ophthalmological images of different magnifications by using the image of the intermediate magnification captured with the decided method.

11. The ophthalmological apparatus according to claim 1, wherein a higher-magnification image, from among the acquired images, is an adaptive optics SLO (Scanning Laser Ophthalmoscope) image and a lower-magnification image, from among the acquired images, is an SLO image without aberration correction.

12. The ophthalmological apparatus according to claim 1, wherein the acquired images include a higher-magnification image and a lower magnification image, and
the alignment unit is configured to align the higher-magnification image with the image of intermediate magnification after the alignment unit aligns the lower-magnification image with the image of intermediate magnification.

13. The ophthalmological apparatus according to claim 12, wherein the higher-magnification image is an adaptive optics SLO (Scanning Laser Ophthalmoscope) image and the lower-magnification image is an SLO image without aberration correction.

* * * * *